(12) United States Patent
Musgrove et al.

(10) Patent No.: US 11,475,998 B2
(45) Date of Patent: Oct. 18, 2022

(54) DATA PREPARATION FOR ARTIFICIAL INTELLIGENCE-BASED CARDIAC ARRHYTHMIA DETECTION

(71) Applicant: Medtronic, Inc., Minneapolis, MN (US)

(72) Inventors: Donald R. Musgrove, Minneapolis, MN (US); Niranjan Chakravarthy, Singapore (SG); Siddharth Dani, Minneapolis, MN (US); Tarek D. Haddad, Minneapolis, MN (US); Andrew Radtke, Minneapolis, MN (US); Rodolphe Katra, Blaine, MN (US); Lindsay A. Pedalty, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 67 days.

(21) Appl. No.: 16/851,500

(22) Filed: Apr. 17, 2020

(65) Prior Publication Data

US 2020/0357518 A1    Nov. 12, 2020

Related U.S. Application Data

(60) Provisional application No. 62/843,702, filed on May 6, 2019.

(51) Int. Cl.
*G16H 50/20* (2018.01)
*G16H 40/60* (2018.01)

(52) U.S. Cl.
CPC ............ *G16H 50/20* (2018.01); *G16H 40/60* (2018.01)

(58) Field of Classification Search
CPC ........ G16H 50/20; G16H 40/60; G16H 40/63; G16H 40/67; A61B 5/352; A61B 5/361;
(Continued)

(56) References Cited

U.S. PATENT DOCUMENTS 4,458,691 A    7/1984  Netravali
6,212,428 B1   4/2001  Hsu et al.
(Continued)

FOREIGN PATENT DOCUMENTS

CN    108030488 A    5/2018
EP    1218060 B1    7/2002
(Continued)

OTHER PUBLICATIONS

Arrobo, An innovative wireless Cardiac Rhythm Management (iCRM) system, 2014, Wireless Telecommunications Symposium, pp. 1-5 (Year: 2014).*

(Continued)

*Primary Examiner* — Joshua B Blanchette
*Assistant Examiner* — Tran N Nguyen
(74) *Attorney, Agent, or Firm* — Shumaker & Sieffert, P.A.

(57) ABSTRACT

Techniques are disclosed for preparing data for use in artificial intelligence (AI)-based cardiac arrhythmia detection. In accordance with the techniques of this disclosure, a computing system may obtain a cardiac electrogram (EGM) strip that represents a waveform of a cardiac rhythm of a same patient. Additionally, the computing system may preprocess the cardiac EGM strip. The computing system may then apply a deep learning model to the preprocessed cardiac EGM strip to generate arrhythmia data indicating whether the cardiac EGM strip represents one or more occurrences of one or more cardiac arrhythmias.

25 Claims, 17 Drawing Sheets

(58) Field of Classification Search
CPC ......... A61B 2560/0209; A61B 5/7264; A61B 5/686; A61B 2560/0242
USPC ...................................................... 705/2–3
See application file for complete search history.

(56) References Cited

U.S. PATENT DOCUMENTS

| | | | |
|---|---|---|---|
| 6,308,094 | B1 | 10/2001 | Shusterman et al. |
| 6,594,523 | B1 | 7/2003 | Levine |
| 8,103,346 | B2 | 1/2012 | Mass et al. |
| 8,521,281 | B2 | 8/2013 | Patel et al. |
| 9,183,351 | B2 | 11/2015 | Shusterman |
| 9,585,590 | B2 | 3/2017 | McNair |
| 9,743,890 | B2 | 8/2017 | Lord et al. |
| 9,775,559 | B2 | 10/2017 | Zhang et al. |
| 10,463,269 | B2 | 11/2019 | Boleyn et al. |
| 2002/0016550 | A1 | 2/2002 | Sweeney et al. |
| 2002/0123768 | A1 | 9/2002 | Gilkerson et al. |
| 2006/0247709 | A1 | 11/2006 | Gottesman et al. |
| 2010/0179444 | A1* | 7/2010 | O'Brien ............... A61B 5/7207 600/509 |
| 2010/0280841 | A1 | 11/2010 | Dong et al. |
| 2011/0270109 | A1* | 11/2011 | Zhang .................... A61B 5/349 600/518 |
| 2012/0209126 | A1 | 8/2012 | Amos et al. |
| 2013/0274524 | A1 | 10/2013 | Dakka et al. |
| 2013/0274624 | A1 | 10/2013 | Mahajan et al. |
| 2014/0257063 | A1 | 9/2014 | Ong et al. |
| 2015/0164349 | A1 | 6/2015 | Gopalakrishnan et al. |
| 2016/0022164 | A1* | 1/2016 | Brockway ............ A61B 5/7203 600/509 |
| 2016/0135706 | A1 | 5/2016 | Sullivan et al. |
| 2016/0192853 | A1 | 7/2016 | Bardy et al. |
| 2016/0220137 | A1 | 8/2016 | Mahajan et al. |
| 2016/0232280 | A1* | 8/2016 | Apte ...................... G16B 50/10 |
| 2017/0105683 | A1 | 4/2017 | Xue |
| 2017/0156592 | A1 | 6/2017 | Fu |
| 2017/0265765 | A1* | 9/2017 | Baumann ............. A61B 5/7264 |
| 2017/0290550 | A1 | 10/2017 | Perschbacher et al. |
| 2017/0347894 | A1 | 12/2017 | Bhushan et al. |
| 2017/0354365 | A1 | 12/2017 | Zhou |
| 2018/0089763 | A1 | 3/2018 | Okazaki |
| 2018/0146874 | A1 | 5/2018 | Walker et al. |
| 2018/0146929 | A1* | 5/2018 | Joo ....................... A61B 5/0816 |
| 2018/0233227 | A1 | 8/2018 | Galloway et al. |
| 2018/0279891 | A1 | 10/2018 | Miao et al. |
| 2019/0008461 | A1 | 1/2019 | Gupta et al. |
| 2019/0029552 | A1 | 1/2019 | Perschbacher et al. |
| 2019/0038148 | A1 | 2/2019 | Valys et al. |
| 2019/0038149 | A1 | 2/2019 | Gopalakrishnan et al. |
| 2019/0209022 | A1* | 7/2019 | Sobol ................... A61B 5/6804 |
| 2019/0275335 | A1 | 9/2019 | Volpe et al. |
| 2019/0378620 | A1 | 12/2019 | Saren |
| 2020/0100693 | A1 | 4/2020 | Velo |
| 2020/0178825 | A1* | 6/2020 | Lu ......................... A61B 5/0245 |
| 2020/0288997 | A1 | 9/2020 | Shute et al. |
| 2020/0352521 | A1 | 11/2020 | Chakravarthy et al. |
| 2020/0353271 | A1 | 11/2020 | Dani et al. |
| 2021/0137384 | A1 | 5/2021 | Robinson et al. |
| 2021/0204858 | A1 | 7/2021 | Attia et al. |
| 2021/0338134 | A1 | 11/2021 | Chakravarthy et al. |
| 2021/0338138 | A1 | 11/2021 | Pedalty et al. |
| 2021/0343416 | A1 | 11/2021 | Chakravarthy et al. |
| 2021/0345865 | A1 | 11/2021 | Spillinger et al. |
| 2021/0358631 | A1 | 11/2021 | Haddad et al. |

FOREIGN PATENT DOCUMENTS

| | | | |
|---|---|---|---|
| EP | 2427105 | A1 | 3/2012 |
| WO | 2010129447 | A1 | 11/2010 |
| WO | 2013/160538 | A1 | 10/2013 |
| WO | 2017072250 | A1 | 5/2017 |
| WO | 2017091736 | A1 | 6/2017 |
| WO | 2018119316 | A1 | 6/2018 |
| WO | 2020049267 | A1 | 3/2020 |

OTHER PUBLICATIONS

Isin, Cardiac arrhythmia detection using deep learning, 2017, Procedia Computer Science, vol. 120, 2017, pp. 268-275 (Year: 2017).*
Swerdlow, Troubleshooting Implanted Cardioverter Defibrillator Sensing Problems I, 2014, Arrhythmia and Electrophysiology. 2014; 7:1237-1261 (Year: 2014).*
Wartzek, ECG on the Road: Robust and Unobtrusive Estimation of Heart Rate, 2011, IEEE Transactions on Biomedical Engineering, vol. 58, No. 11, pp. 3112-3120 (Year: 2011).*
Chen, Electrocardiogram Recognition Based on Variational AutoEncoder, Aug. 29, 2018, Machine Learning and Biometrics. IntechOpen (Year: 2018).*
International Search Report and Written Opinion of International Application No. PCT/US2020/028925, dated Jul. 15, 2020, 18 pp.
Andersen et al., "A Deep Learning Approach for Real-Time Detection of Atrial Fibrillation," Expert Systems with Applications, vol. 114, Aug. 14, 2018, pp. 465-473.
Schirrmeister et al., "Deep Learning with Convolutional Neural Networks for Brain Mapping and Decoding of Movement-Related Information from the Human EEG," Cornell University Library, Mar. 16, 2017, 58 pp.
Madani et al., "Fast and Accurate View Classification of Echocardiograms Using Deep Learning," Nature Partner Journals, vol. 1, No. 6, Mar. 21, 2018, 8 pp.
U.S. Appl. No. 16/850,699, filed Apr. 16, 2020 by Chakravarthy et al.
U.S. Appl. No. 16/851,603, filed Apr. 17, 2020 by Chakravarthy et al.
U.S. Appl. No. 16/850,749, filed Apr. 16, 2020 by Pedalty et al.
"Classify ECG Signals Using Long Short-Term Memory Networks," MATLAB, retrieved from https://www.mathworks.com/help/signal/examples/classify-ecg-signals-using-long-short-term-memory-networks.html, Nov. 2, 2018, 19 pp.
"Visualize Features of a Convolutional Neural Network," MATLAB & Simulink, Mar. 15, 2018, 9 pp.
Fawaz et al., "Deep learning for time series classification: a review," Irirrmas, Universite Haute Alsace, Dec. 7, 2018, 53 pp.
Kelwade et al., "Prediction of Cardiac Arrhythmia using Artificial Neural Network," International Journal of Computer Applications (0975-8887), vol. 115—No. 20, Apr. 2015, 6 pp.
Lau et al., "Connecting the Dots: From Big Data to Healthy Heart," Circulation, vol. 134, No. 5, Aug. 2, 2017, 5 pp.
Schwab et al., "Beat by Beat: Classifying Cardiac Arrhythmias with Recurrent Neural Networks," 2017 Computing in Cardiology (CinC), vol. 44, Oct. 24, 2017, 4 pp.
U.S. Appl. No. 16/593,739, filed Oct. 4, 2019 by Haddad et al.
U.S. Appl. No. 16/832,732, filed Mar. 27, 2020 by Chakravarthy et al.
U.S. Appl. No. 16/845,996, filed Apr. 10, 2020 by Haddad et al.
"Visualize Features of a Convolutional Neural Network," MATLAB & Simulink, retrieved from https://www.mathworks.com/help/deeplearning/examples/visualize-features-of-a-convolutional-neural-network.html, Sep. 11, 2019, 7 pp.
International Preliminary Report on Patentability from International Application No. PCT/US2020/028925, dated Nov. 2, 2021, 8 pp.
Notice of Allowance from U.S. Appl. No. 17/389,831, dated Jan. 5, 2022, 5 pp.
Office Action from U.S. Appl. No. 17/389,831, dated Sep. 10, 2021, 22 pp.
Amendment in Response to Office Action dated Sep. 10, 2021, from U.S. Appl. No. 17/389,831, filed Dec. 10, 2021, 17 pp.
Anonymous, "Receiver Operating Characteristic-Wikipedia," Mar. 20, 2019, Retrieved from the Internet: URL: https://en.wikipedia.org/w/index.php?title=Receiver_operating_characteristic&oldis=888671034#History, 12 pp.
Bresnick, "Machine Learning Algorithm Outperforms Cardiologists Reading EKGs", Health IT Analytics, Jul. 12, 2017, 5 pp.
Habibzadeh et al., "On Determining the Most Appropriate Test Cut-Off Value: the Case of Tests with Continuous Results," Biochemia Medica, Oct. 15, 2016, pp. 297-307.
Notice of Allowance from U.S. Appl. No. 17/389,831, dated Apr. 25, 2022, 5 pp.

(56) References Cited

OTHER PUBLICATIONS

Office Action from U.S. Appl. No. 16/832,732, dated Mar. 2, 2022, 16 pp.
Response to Office Action dated Mar. 2, 2022, from U.S. Appl. No. 16/832,732, filed May 23, 2022, 10 pp.

* cited by examiner

DATA PREPARATION FOR ARTIFICIAL INTELLIGENCE-BASED CARDIAC ARRHYTHMIA DETECTION

This application claims the benefit of U.S. Provisional Patent Application No. 62/843,702, filed May 6, 2019, the entire content of which is incorporated herein by reference.

FIELD

This disclosure generally relates to health monitoring and, more particularly, to monitoring cardiac health.

BACKGROUND

Malignant tachyarrhythmia, for example, ventricular fibrillation, is an uncoordinated contraction of the cardiac muscle of the ventricles in the heart and is the most commonly identified arrhythmia in cardiac arrest patients. If this arrhythmia continues for more than a few seconds, it may result in cardiogenic shock and cessation of effective blood circulation. Consequently, sudden cardiac death (SCD) may result in a matter of minutes.

An implanted or non-implanted medical device may monitor a patient's heart for cardiac arrhythmias. A user, such as a physician, may review data generated by the medical device for cardiac arrhythmias. The user may diagnose a medical condition of the patient based on the cardiac arrhythmias.

SUMMARY

In general, the disclosure describes techniques for preparing data for use in artificial intelligence (AI)-based cardiac arrhythmia detection. As described herein, a computing system may obtain a cardiac electrogram (EGM) strip that represents a waveform of a cardiac rhythm of a patient. Additionally, the computing system may preprocess the cardiac EGM strip. The computing system may then apply a deep learning model to the preprocessed cardiac EGM strip to generate arrhythmia data indicating whether the cardiac EGM strip represents one or more occurrences of one or more cardiac arrhythmias.

In one aspect, this disclosure describes a method comprising: obtaining, by a computing system, one or more cardiac electrogram (EGM) strips that represent a waveform of a cardiac rhythm of a patient; preprocessing, by the computing system, the one or more cardiac EGM strips; and applying, by the computing system, a deep learning model to the one or more preprocessed cardiac EGM strips to generate arrhythmia data indicating whether the one or more cardiac EGM strips represent one or more occurrences of one or more cardiac arrhythmias.

In another aspect, this disclosure describes a computing system comprising: a storage device configured to store one or more cardiac electrogram (EGM) strips that represent a waveform of a cardiac rhythm of a patient; one or more processing circuits configured to: preprocess the one or more cardiac EGM strips; and apply a deep learning model to the one or more preprocessed cardiac EGM strips to generate arrhythmia data indicating whether the one or more cardiac EGM strips represent one or more occurrences of one or more cardiac arrhythmias.

In another aspect, this disclosure describes a computer-readable storage medium having instructions stored thereon that, when executed, cause a computing system to obtain one or more cardiac electrogram (EGM) strips that represent a waveform of a cardiac rhythm of a patient; preprocess the one or more cardiac EGM strips; and apply a deep learning model to the one or more preprocessed cardiac EGM strips to generate arrhythmia data indicating whether the one or more cardiac EGM strips represent one or more occurrences of one or more cardiac arrhythmias.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

BRIEF DESCRIPTION OF DRAWINGS

Like reference characters refer to like elements throughout the figures and description.

DETAILED DESCRIPTION

Figure 1:
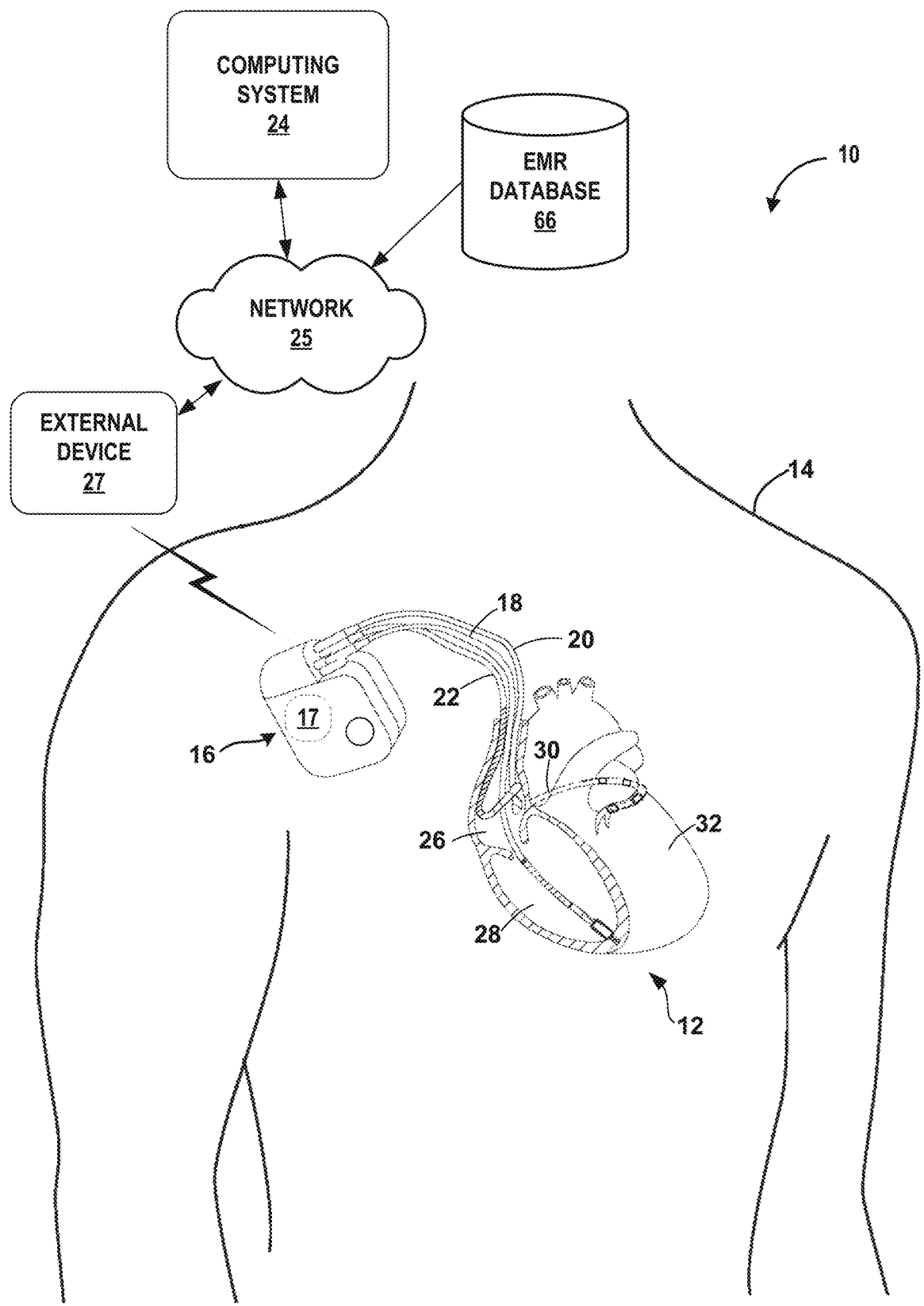
FIG. 1 is a block diagram illustrating a system for analyzing one or more aspects of a cardiac rhythm of a patient in accordance with one or more techniques of the disclosure.

FIG. 1 is a block diagram illustrating a system 10 for analyzing one or more aspects of a cardiac rhythm of a patient 14 in accordance with the techniques of the disclosure. System 10 includes a medical device 16. One example of such a medical device is an implantable medical device (IMD), as shown in FIG. 1. As illustrated by example system 10 in FIG. 1, medical device 16 may, in some examples, be an implantable cardiac monitor, an implantable cardiac pacemaker, implantable cardioverter/defibrillator (ICD), or pacemaker/cardioverter/defibrillator, for example. In some examples, medical device 16 is a non-implantable medical device, such as a non-implantable cardiac monitor (e.g., a Holter monitor).

In the example of FIG. 1, medical device 16 is connected to leads 18, 20 and 22 and is communicatively coupled to external device 27, which in turn is communicatively coupled to computing system 24 over communication network 25. Medical device 16 senses electrical signals attendant to the depolarization and repolarization of heart 12, e.g., a cardiac electrogram (EGM), via electrodes on one or more leads 18, 20 and 22 or the housing of medical device 16. Medical device 16 may also deliver therapy in the form of electrical signals to heart 12 via electrodes located on one or more leads 18, 20 and 22 or a housing of medical device 16. The therapy may be pacing, cardioversion and/or defibrillation pulses. Medical device 16 may monitor cardiac EGM signals collected by electrodes on leads 18, 20 or 22, and based on the cardiac EGM signal, diagnose, and treat cardiac arrhythmias.

In some examples, medical device 16 includes communication circuitry 17 including any suitable circuitry, firmware, software, or any combination thereof for communicating with another device, such as external device 27 of FIG. 1. For example, communication circuitry 17 may include one or more processors, memory, wireless radios, antennae, transmitters, receivers, modulation and demodulation circuitry, filters, amplifiers, or the like for radio frequency communication with other devices, such as computing system 24. Medical device 16 may use communication circuitry 17 to receive downlinked data to control one or more operations of medical device 16 and/or send uplinked data to external device 27.

Leads 18, 20, 22 extend into the heart 12 of patient 14 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

While example system 10 of FIG. 1 depicts medical device 16, in other examples, the techniques of the disclosure may be applied to other types of medical devices that are not necessarily implantable. For example, a medical device in accordance with the techniques of the disclosure may include a wearable medical device or "smart" apparel worn by patient 14. For example, such a medical device may take the form of a wristwatch worn by patient 14 or circuitry that is adhesively affixed to patient 14. In another example, a medical device as described herein may include an external medical device with implantable electrodes.

In some examples, external device 27 takes the form of an external programmer or mobile device, such as a mobile phone, a "smart" phone, a laptop, a tablet computer, a personal digital assistant (PDA), etc. In some examples, external device 27 is a CareLink™ monitor available from Medtronic, Inc. A user, such as a physician, technician, surgeon, electro-physiologist, or other clinician, may interact with external device 27 to retrieve physiological or diagnostic information from medical device 16. A user, such as patient 14 or a clinician as described above, may also interact with external device 27 to program medical device 16, e.g., select or adjust values for operational parameters of medical device 16. External device 27 may include processing circuitry, a memory, a user interface, and communication circuitry capable of transmitting and receiving information to and from each of medical device 16 and computing system 24.

In some examples, computing system 24 takes the form of a handheld computing device, computer workstation, server or other networked computing device, smartphone, tablet, or external programmer that includes a user interface for presenting information to and receiving input from a user. In some examples, computing system 24 may include one or more devices that implement a machine learning system, such as a neural network, a deep learning system, or another type of machine learning system. A user, such as a physician, technician, surgeon, electro-physiologist, or other clinician, may interact with computing system 24 to retrieve physiological or diagnostic information from medical device 16. A user may also interact with computing system 24 to program medical device 16, e.g., select values for operational parameters of the IMD. Computing system 24 may include a processor configured to evaluate cardiac EGMs (or segments thereof) and/or other sensed signals transmitted from medical device 16 to computing system 24.

Network 25 may include one or more computing devices (not shown), such as one or more non-edge switches, routers, hubs, gateways, security devices such as firewalls, intrusion detection, and/or intrusion prevention devices, servers, computer terminals, laptops, printers, databases, wireless mobile devices such as cellular phones or personal digital assistants, wireless access points, bridges, cable modems, application accelerators, or other network devices. Network 25 may include one or more networks administered by service providers and may thus form part of a large-scale public network infrastructure, e.g., the Internet. Network 25 may provide computing devices, such as computing system 24 and medical device 16, access to the Internet, and may provide a communication framework that allows the computing devices to communicate with one another. In some examples, network 25 may be a private network that provides a communication framework that allows computing system 24, medical device 16, and EMR database 66 to communicate with one another but isolates computing system 24, medical device 16, and EMR database 66 from external devices for security purposes. In some examples, the communications between computing system 24, medical device 16, and EMR database 66 are encrypted.

External device 27 and computing system 24 may communicate via wireless or non-wireless communication over network 25 using any techniques known in the art. In some examples, computing system 24 is a remote device that communicates with external device 27 via an intermediary device located in network 25, such as a local access point, wireless router, or gateway. While in the example of FIG. 1, external device 27 and computing system 24 communicate over network 25, in some examples, external device 27 and computing system 24 communicate with one another directly. Examples of communication techniques may include, for example, communication according to the Bluetooth® or BLE protocols. Other communication techniques are also contemplated. Computing system 24 may also communicate with one or more other external devices using a number of known communication techniques, both wired and wireless.

EMR database 66 stores EMR data for patient 14. EMR database 66 may include processing circuitry and one or more storage mediums (e.g., random access memory (RAM), read only memory (ROM), programmable read only memory (PROM), erasable programmable read only memory (EPROM), electronically erasable programmable read only memory (EEPROM), or flash memory. In some examples, EMR database 66 is a cloud computing system. In some examples, the functions of EMR database 66 are distributed across a number of computing systems.

In one example, computing system 24 receives patient data collected by medical device 16 of patient 14. In some examples, the patient data includes physiological data for patient 14, such as one or more of an activity level of patient 14, a heart rate of patient 14, a posture of patient 14, a cardiac electrogram of patient 14, a blood pressure of patient 14, a pulse transit time of patient 14, a respiration rate of patient 14, a hypopnea index or apnea of patient 14, accelerometer data for patient 14, features derived from accelerometer data of patient 14, such as activity counts, posture, statistical control process variables, etc., a raw electromyogram or cardiac EGM of patient 14, one or more features derived from a raw electromyogram of patient 14, such as heart rate variability, t-wave alternans, QRS morphology, etc., interval data and features derived from interval data, heart sounds, potassium levels, glycemic index, a temperature of patient 14, or any data derivable from the aforementioned parametric data, or any other types of patient parametric data. In some examples, medical device 16 or another device may automatically generate the patient parametric data by processing information from one or more sensors. For example, medical device 16 may determine, via one or more sensors, that patient 14 has fallen down, patient 14 is frail or suffers an illness, or that patient 14 is suffering an instance of sleep apnea.

In some examples, the patient data includes environmental data such as, air quality measurements, ozone levels, particulate counts, or pollution levels proximate to patient 14, an ambient temperature, or daylight hours. In some examples, one of medical device or external device 27 may sense, via one or more sensors, the environmental data. In another example, the environmental data is received by external device 27 via an application, such as a weather application, executing on external device 27, and uploaded to computing system 24 over network 25. In another example, computing system 24 collects the environmental data directly from a cloud service that has location-based data for patient 14.

In some examples, the patient data includes patient symptom data that is uploaded by patient 14 via an external device, such as external device 27. For example, patient 14 may upload the patient symptom data via an application executing on a smart phone. In some examples, patient 14 may upload the patient symptom data via a user interface (not depicted in FIG. 1), such as by touchscreen, keyboard, graphical user interface, voice commands, etc.

In some examples, the patient data includes device-related data, such as one or more of an impedance of one or more electrodes of the medical device, a selection of electrodes, a drug delivery schedule for the medical device, a history of electrical pacing therapy delivered to the patient, or diagnostic data for the medical device. In some examples, the medical device that collects the patient data is an IMD. In other examples, the medical device that collects the patient data is another type of patient device, such as a wearable medical device or a mobile device (e.g., a smartphone) of patient 14. In some examples, computing system 24 receives the patient data on a periodic, e.g., daily, basis.

In some examples, computing system 24 further receives EMR data for patient 14 from EMR database 66. The EMR data may be considered another form of patient data. In some examples, the EMR data stored by EMR database 66 may include many different types of historical medical information about patient 14. For example, EMR database 66 may store a medication history of the patient, a surgical procedure history of the patient, a hospitalization history of the patient, potassium levels of the patient over time, one or more lab test results for patient 14, a cardiovascular history of patient 14, or co-morbidities of patient 14 such as atrial fibrillation, heart failure, or diabetes, as examples.

Computing system 24 may implement a cardiac EGM monitoring system that may aid in the management of chronic cardiac disease. In accordance with a technique of this disclosure, to implement the cardiac EGM monitoring system, computing system 24 may apply artificial intelligence (AI) techniques to analyze patient data, such as cardiac EGM data. Example AI techniques may include deep learning or other machine learning techniques. Neural network algorithms are one example of deep learning algorithms.

An AI system is a computing system that comprises a memory and one or more processing circuits configured to perform AI techniques. In the context of FIG. 1, the AI system may be medical device 16, computing system 24, external device 27, or another device or system of devices. Thus, in this disclosure, discussion of actions performed by the AI system may apply to actions performed by any of these devices, unless otherwise indicated.

The AI system may generate data regarding one or more aspects of the cardiac rhythm of patient 14. For instance, the AI system may generate, based at least in part on cardiac EGM strips obtained from one or more medical devices, such as medical device 16, arrhythmia data that indicating whether the cardiac EGM strip represents one or more occurrences of one or more cardiac arrhythmias. A cardiac EGM strip comprises data representing a cardiac rhythm of a patient in a contiguous time period (e.g., 30 seconds, 45 seconds, etc.). A cardiac EGM strip may comprise a series of samples representing a waveform of the cardiac rhythm. A user (e.g., a technician, physician, patient, healthcare professional, or other type of user) may review the detected occurrences of the one or more cardiac arrhythmias for diagnostic purposes or as part of performing ongoing care of patient 14. In addition to cardiac EGM strips, the AI system may use one or more other types of patient data to detect occurrences of cardiac arrhythmias, such as information from an electronic medical record of patient 14.

The AI system may be trained to identify one or more aspects of the cardiac rhythm of patient 14 that are of interest in a given cardiac EGM strip by applying one or more deep learning models that have been trained to identify such aspects of the cardiac rhythm of patient 14. The aspects of the cardiac rhythm of patient 14 may include various cardiac arrhythmias, locations of such cardiac arrhythmias within one or more cardiac EGM strips (which reflects the time of occurrence of the arrhythmia), morphological aspects of occurrences of cardiac arrhythmias, and so on. The cardiac rhythm classification model may be trained on cardiac EGM strips drawn from a population of subjects, individual patients, cohorts of patients, and, in some examples, other data.

The performance of the deep learning model may be improved by preprocessing the input data provided to the deep learning model. For instance, as described in this disclosure, preprocessing the data may enable the deep learning model to be used with cardiac EGM strips generated by multiple types of devices. Thus, in accordance with the techniques of this disclosure, the AI system may obtain a cardiac EGM strip that represents a waveform of a cardiac rhythm of a patient. Additionally, the AI system may preprocess the cardiac EGM strip. The computing system may then apply a deep learning model to the preprocessed cardiac EGM strip to generate arrhythmia data indicating whether the cardiac EGM strip represents one or more occurrences of one or more cardiac arrhythmias. For instance, the deep learning system may be trained to generate arrhythmia data that comprises a vector of elements corresponding to different cardiac arrhythmias. The value of an element in the vector indicates whether an occurrence of the corresponding cardiac arrhythmia happened in the cardiac EGM strip.

Figure 2:
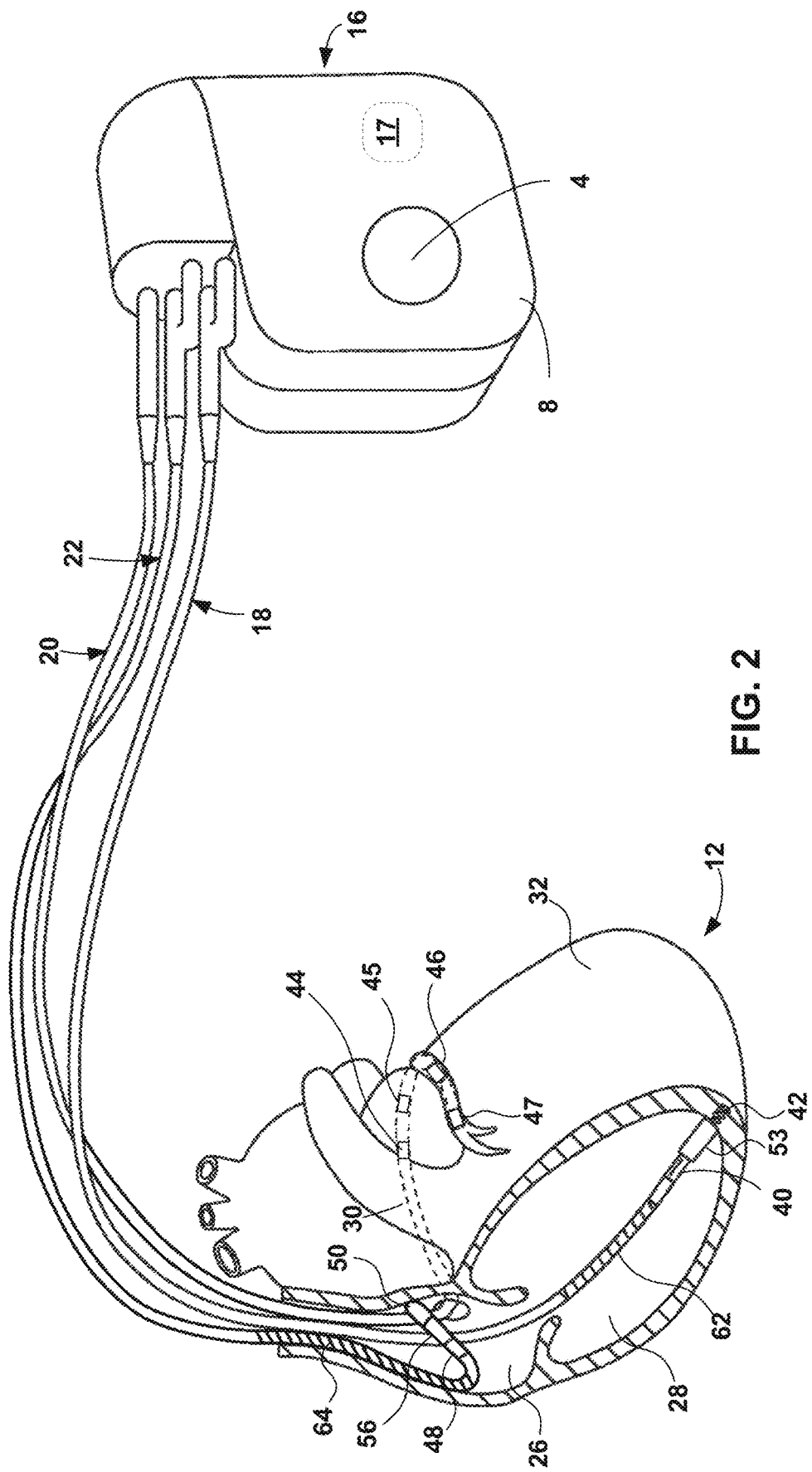
FIG. 2 is a conceptual diagram illustrating an implantable medical device (IMD) and leads of the system of FIG. 1 in greater detail.

FIG. 2 is a conceptual diagram illustrating medical device 16 and leads 18, 20, 22 of system 10 of FIG. 1 in greater detail. In the illustrated example, bipolar electrodes 40 and 42 are located adjacent to a distal end of lead 18, and bipolar electrodes 48 and 50 are located adjacent to a distal end of lead 22. In addition, four electrodes 44, 45, 46 and 47 are located adjacent to a distal end of lead 20. Lead 20 may be referred to as a quadrapolar LV lead. In other examples, lead 20 may include more or fewer electrodes. In some examples, LV lead 20 comprises segmented electrodes, e.g., in which each of a plurality of longitudinal electrode positions of the lead, such as the positions of electrodes 44, 45, 46 and 47, includes a plurality of discrete electrodes arranged at respective circumferential positions around the circumference of lead.

In the illustrated example, electrodes 40 and 44-48 take the form of ring electrodes, and electrodes 42 and 50 may take the form of extendable helix tip electrodes mounted retractably within insulative electrode heads 52 and 56, respectively. Leads 18 and 22 also include elongated electrodes 62 and 64, respectively, which may take the form of a coil. In some examples, each of electrodes 40, 42, 44-48, 50, 62, and 64 is electrically coupled to a respective conductor within the lead body of its associated lead 18, 20, 22 and thereby coupled to circuitry within medical device 16.

In some examples, medical device 16 includes one or more housing electrodes, such as housing electrode 4 illustrated in FIG. 2, which may be formed integrally with an outer surface of hermetically-sealed housing 8 of medical device 16 or otherwise coupled to housing 8. In some examples, housing electrode 4 is defined by an uninsulated portion of an outward facing portion of housing 8 of medical device 16. Other divisions between insulated and uninsulated portions of housing 8 may be employed to define two or more housing electrodes. In some examples, a housing electrode comprises substantially all of housing 8.

Housing 8 encloses signal generation circuitry that generates therapeutic stimulation, such as cardiac pacing, cardioversion, and defibrillation pulses, as well as sensing circuitry for sensing electrical signals attendant to the depolarization and repolarization of heart 12. Housing 8 may also enclose a memory for storing the sensed electrical signals. Housing 8 may also enclose communication circuitry 17 for communication between medical device 16 and computing system 24.

Medical device 16 senses electrical signals attendant to the depolarization and repolarization of heart 12 via electrodes 4, 40, 42, 44-48, 50, 62, and 64. Medical device 16 may sense such electrical signals via any bipolar combination of electrodes 40, 42, 44-48, 50, 62, and 64. Furthermore, any of the electrodes 40, 42, 44-48, 50, 62, and 64 may be used for unipolar sensing in combination with housing electrode 4.

The illustrated numbers and configurations of leads 18, 20 and 22 and electrodes are merely examples. Other configurations, i.e., number and position of leads and electrodes, are possible. In some examples, system 10 may include an additional lead or lead segment having one or more electrodes positioned at different locations in the cardiovascular system for sensing and/or delivering therapy to patient 14. For example, instead of or in addition to intercardiac leads 18, 20 and 22, system 10 may include one or more epicardial or extravascular (e.g., subcutaneous or substernal) leads not positioned within heart 12.

Medical device 16 may send patient data to computing system 24 (e.g., by way of external device 27). The patient data may include data based on the electrical signals detected by electrodes 4, 40, 42, 44-48, 50, 62, and/or 64. For example, medical device 16 may gather and send cardiac EGM data to computing system 24. In accordance with the techniques of this disclosure, an AI system, which may be implemented by computing system 24, medical device 16, or another device, may preprocess the patient data and use the preprocessed patient data to determine generate arrhythmia data or other data about a cardiac rhythm of patient 14. In some examples, medical device 16 may preprocess cardiac EGM strips and computing system 24 or external device 27 may apply a deep learning model to the preprocessed cardiac EGM strips to generate arrhythmia data.

Although described herein in the context of an example medical device 16 that provides therapeutic electrical stimulation, the techniques disclosed herein may be used with other types of devices. For example, the techniques may be implemented with an extra-cardiac defibrillator coupled to electrodes outside of the cardiovascular system, a transcatheter pacemaker configured for implantation within the heart, such as the Micra™ transcatheter pacing system commercially available from Medtronic PLC of Dublin, Ireland, an insertable cardiac monitor, such as the Reveal LINQ™ ICM, also commercially available from Medtronic PLC, a neurostimulator, a drug delivery device, a wearable device such as a wearable cardioverter defibrillator, a fitness tracker, or other wearable device, a mobile device, such as a mobile phone, a "smart" phone, a laptop, a tablet computer, a personal digital assistant (PDA), or "smart" apparel such as "smart" glasses or a "smart" watch.

Figure 3:
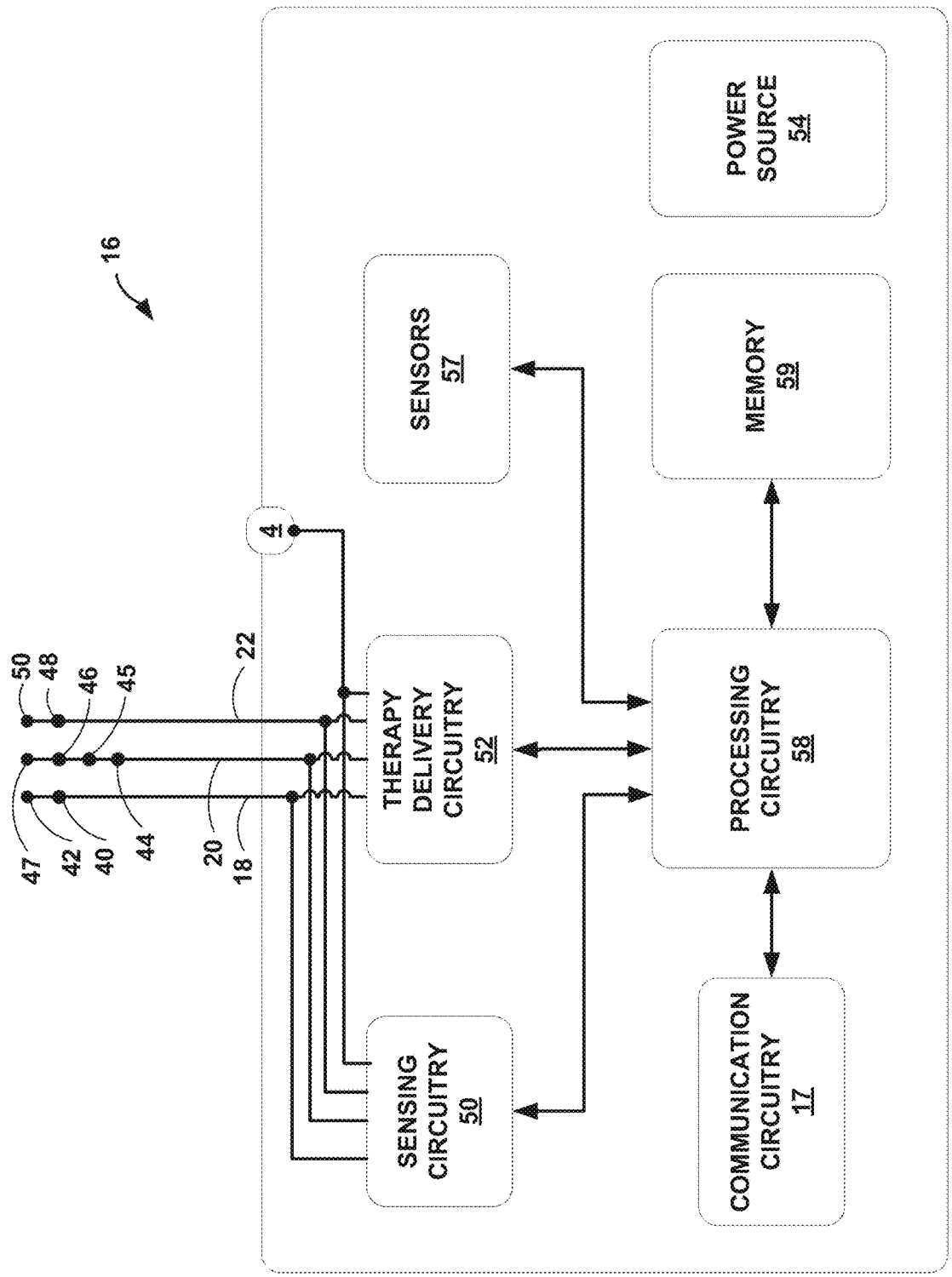
FIG. 3 is a block diagram of an example implantable medical device according to one or more techniques of the disclosure.

FIG. 3 is a block diagram of example medical device 16 according to the techniques of the disclosure. In the illustrated example, medical device 16 includes processing circuitry 58, memory 59, communication circuitry 17, sensing circuitry 50, therapy delivery circuitry 52, sensors 57, and power source 54. Memory 59 includes computer-readable instructions that, when executed by processing circuitry 58, cause medical device 16 and processing circuitry 58 to perform various functions attributed to medical device 16 and processing circuitry 58 herein (e.g., performing short-term prediction of cardiac arrhythmias, delivering therapy, such as anti-tachycardia pacing, bradycardia pacing, and post-shock pacing therapy, etc.). Memory 59 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processing circuitry 58 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 58 may include multiple components, such as any combination of one or more microprocessors, one or more controllers, one or more DSPs, one or more ASICs, or one or more FPGAs, as well as other discrete or integrated logic circuitry. The functions attributed to processing circuitry 58 herein may be embodied as software, firmware, hardware or any combination thereof.

Processing circuitry 58 controls therapy delivery circuitry 52 to deliver stimulation therapy to heart 5 according to therapy parameters, which may be stored in memory 59. For example, processing circuitry 58 may control therapy delivery circuitry 52 to deliver electrical pulses with the amplitudes, pulse widths, frequency, or electrode polarities specified by the therapy parameters. In this manner, therapy delivery circuitry 52 may deliver pacing pulses (e.g., ATP pulses, bradycardia pacing pulses, or post-shock pacing therapy) to heart 5 via electrodes 34 and 40. In some examples, therapy delivery circuitry 52 may deliver pacing stimulation, e.g., ATP therapy, bradycardia therapy, or post-shock pacing therapy, in the form of voltage or current electrical pulses. In other examples, therapy delivery circuitry 52 may deliver one or more of these types of stimulation in the form of other signals, such as sine waves, square waves, or other substantially continuous time signals.

Therapy delivery circuitry 52 is electrically coupled to electrodes 34 and 40 carried on the housing of medical device 16. Although medical device 16 may only include two electrodes, e.g., electrodes 34 and 40, in other examples, medical device 16 may utilize three or more electrodes. Medical device 16 may use any combination of electrodes to deliver therapy and/or detect electrical signals from patient 12. In some examples, therapy delivery circuitry 52 includes a charging circuit, one or more pulse generators, capacitors, transformers, switching modules, and/or other components capable of generating and/or storing energy to deliver as pacing therapy, cardiac resynchronization therapy, other therapy or a combination of therapies. In some examples, therapy delivery circuitry 52 delivers therapy as one or more electrical pulses according to one or more therapy parameter sets defining an amplitude, a frequency, a voltage or current of the therapy, or other parameters of the therapy.

Sensing circuitry 50 monitors signals from one or more combinations (also referred to as vectors) of two or more electrodes from among electrodes 4, 40, 42, 44-48, 50, 62 (FIG. 2), and 64 (FIG. 2) in order to monitor electrical activity of heart 12, impedance, or other electrical phenomenon. In some examples, sensing circuitry 50 includes one or more analog components, digital components or a combination thereof. In some examples, sensing circuitry 50 includes one or more sense amplifiers, comparators, filters, rectifiers, threshold detectors, analog-to-digital converters (ADCs) or the like. In some examples, sensing circuitry 50 converts sensed signals to digital form and provides the digital signals to processing circuitry 58 for processing or analysis. In one example, sensing circuitry 50 amplifies signals from electrodes 4, 40, 42, 44-48, 50, 62, and 64 and converts the amplified signals to multi-bit digital signals by an ADC.

In some examples, sensing circuitry 50 performs sensing of the cardiac electrogram to determine heart rates or heart rate variability, or to detect arrhythmias (e.g., tachyarrhythmias or bradycardia) or to sense other parameters or events from the cardiac electrogram. Sensing circuitry 50 may also include switching circuitry to select which of the available electrodes (and the electrode polarity) are used to sense the heart activity, depending upon which electrode combination, or electrode vector, is used in the current sensing configuration. Processing circuitry 58 may control the switching circuitry to select the electrodes that function as sense electrodes and their polarity. Sensing circuitry 50 may include one or more detection channels, each of which may be coupled to a selected electrode configuration for detection of cardiac signals via that electrode configuration. In some examples, sensing circuitry 50 compares processed signals to a threshold to detect the existence of atrial or ventricular depolarizations and indicate the existence of the atrial depolarization (e.g., P-waves) or ventricular depolarizations (e.g., R-waves) to processing circuitry 58. Sensing circuitry 50 may comprise one or more amplifiers or other circuitry for comparison of the cardiac electrogram amplitude to a threshold, which may be adjustable.

Processing circuitry 58 may include a timing and control module, which may be embodied as hardware, firmware, software, or any combination thereof. The timing and control module may comprise a dedicated hardware circuit, such as an ASIC, separate from other processing circuitry 58 components, such as a microprocessor, or a software module executed by a component of processing circuitry 58, which may be a microprocessor or ASIC. The timing and control module may implement programmable counters. If medical device 16 is configured to generate and deliver bradycardia pacing pulses to heart 12, such counters may control the basic time intervals associated with DDD, VVI, DVI, VDD, AAI, DDI, DDDR, VVIR, DVIR, VDDR, AAIR, DDIR and other modes of pacing.

In some examples, processing circuitry 58 of medical device 16 implements AI system 300. For instance, processing circuitry 58 may apply a deep learning model to cardiac EGM strips, as described elsewhere in this disclosure. Processing circuitry 58 may implement AI system 300 using special-purpose circuitry or by executing software instructions stored on a computer-readable medium, such as memory 59. Sensing circuitry 50 may generate cardiac EGM strips based on data received from electrodes 4, 40, 42, 44-48, 50, 62, and 64. Communication circuitry 17 may transmit cardiac EGM strips and/or other data to external device 27.

Memory 59 may be configured to store a variety of operational parameters, therapy parameters, sensed and detected data, and any other information related to the therapy and treatment of patient 12. In the example of FIG.

3, memory 59 may store sensed cardiac EGMs, e.g., associated with detected or predicted arrhythmias, and therapy parameters that define the delivery of therapy provided by therapy delivery circuitry 52. In other examples, memory 59 may act as a temporary buffer for storing data until it can be uploaded to computing system 24.

Communication circuitry 17 includes any suitable circuitry, firmware, software, or any combination thereof for communicating with another device, such as computing system 24 via network 25 of FIG. 1. For example, communication circuitry 17 may include one or more antennae, modulation and demodulation circuitry, filters, amplifiers, or the like for radio frequency communication with other devices, such as computing system 24 via network 25. Under the control of processing circuitry 58, communication circuitry 17 may receive downlink telemetry from and send uplink telemetry to computing system 24 with the aid of an antenna, which may be internal and/or external. Processing circuitry 58 may provide the data to be uplinked to computing system 24 and the control signals for the telemetry circuit within communication circuitry 17, e.g., via an address/data bus. In some examples, communication circuitry 17 may provide received data to processing circuitry 58 via a multiplexer.

Power source 54 may be any type of device that is configured to hold a charge to operate the circuitry of medical device 16. Power source 54 may be provided as a rechargeable or non-rechargeable battery. In other examples, power source 54 may incorporate an energy scavenging system that stores electrical energy from movement of medical device 16 within patient 12.

In accordance with the techniques of the disclosure, medical device 16 collects, via sensing circuitry 50 and/or sensors 57, patient data of patient 14. Sensors 57 may include one or more sensors, such as one or more accelerometers, pressure sensors, optical sensors for O2 saturation, etc. In some examples, the patient data includes one or more of an activity level of patient 14, a heart rate of patient 14, a posture of patient 14, a cardiac electrogram of patient 14 (e.g., cardiac EGM strips of patient 14), a blood pressure of patient 14, accelerometer data for patient 14, or other types of patient parametric data. Medical device 16 uploads, via communication circuitry 17, the patient parametric data to computing system 24 over network 25. In some examples, medical device 16 uploads the patient parametric data to computing system 24 on a daily basis. In some examples, the patient parametric data includes one or more values that represent average measurements of patient 14 over a long-term time period (e.g., about 24 hours to about 48 hours). For example, one or more other devices, such as a wearable medical device or a mobile device (e.g., a smartphone) of patient 14, may collect the patient parametric data and upload the patient parametric data to external device 27 and/or computing system 24.

Although described herein in the context of example medical device 16 that provides therapeutic electrical stimulation, the techniques for short-term prediction of cardiac arrhythmia disclosed herein may be used with other types of devices. For example, the techniques may be implemented with a transcatheter pacemaker configured for implantation within the heart, such as the Micra™ transcatheter pacing system commercially available from Medtronic PLC of Dublin Ireland, an insertable cardiac monitor, such as the Reveal LINQ™ ICM, also commercially available from Medtronic PLC, a neurostimulator, a drug delivery device, a wearable device such as a wearable cardioverter defibrillator, a fitness tracker, or other wearable device, a mobile device, such as a mobile phone, a "smart" phone, a laptop, a tablet computer, a personal digital assistant (PDA), or "smart" apparel such as "smart" glasses or a "smart" watch.

Figure 4:
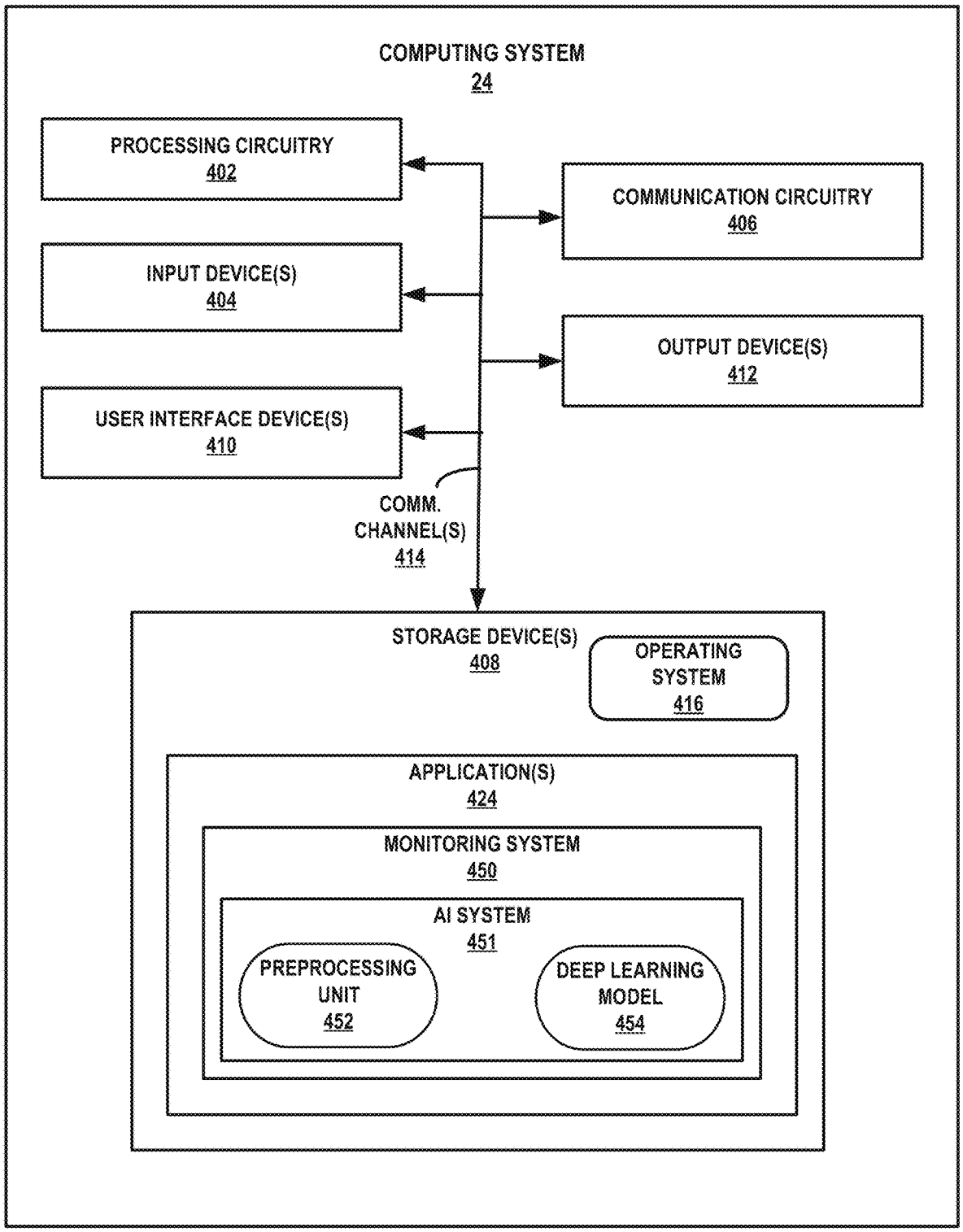
FIG. 4 is a block diagram illustrating an example computing device that operates in accordance with one or more techniques of the present disclosure.

FIG. 4 is a block diagram illustrating an example computing system 24 that operates in accordance with one or more techniques of the present disclosure. In one example, computing system 24 includes processing circuitry 402 for executing applications 424 that include monitoring system 450 or any other applications described herein. Although shown in FIG. 4 as a stand-alone computing system 24 for purposes of example, computing system 24 may be any component or system that includes processing circuitry or other suitable computing environment for executing software instructions and, for example, need not necessarily include one or more elements shown in FIG. 4 (e.g., communication circuitry 406; and in some examples components such as storage device(s) 408 may not be co-located or in the same chassis as other components). In some examples, computing system 24 may be a cloud computing system distributed across a plurality of devices.

As shown in the example of FIG. 4, computing system 24 includes processing circuitry 402, one or more input devices 404, communication circuitry 406, one or more output devices 412, one or more storage devices 408, and user interface (UI) device(s) 410. Computing system 24, in one example, further includes one or more application(s) 424 such as monitoring system 450, and operating system 416 that are executable by computing system 24. Each of components 402, 404, 406, 408, 410, and 412 are coupled (physically, communicatively, and/or operatively) for inter-component communications. In some examples, communication channels 414 may include a system bus, a network connection, an inter-process communication data structure, or any other method for communicating data. As one example, components 402, 404, 406, 408, 410, and 412 may be coupled by one or more communication channels 414.

Processing circuitry 402, in one example, is configured to implement functionality and/or process instructions for execution within computing system 24. For example, processing circuitry 402 may be capable of processing instructions stored in storage device 408. Examples of processing circuitry 402 may include any one or more of a microprocessor, a controller, a digital signal processor (DSP), an application specific integrated circuit (ASIC), a field-programmable gate array (FPGA), or equivalent discrete or integrated logic circuitry.

One or more storage devices 408 may be configured to store information within computing system 24 during operation. Storage device 408, in some examples, is described as a computer-readable storage medium. In some examples, storage device 408 is a temporary memory, meaning that a primary purpose of storage device 408 is not long-term storage. Storage device 408, in some examples, is described as a volatile memory, meaning that storage device 408 does not maintain stored contents when the computer is turned off. Examples of volatile memories include random access memories (RAM), dynamic random access memories (DRAM), static random access memories (SRAM), and other forms of volatile memories known in the art. In some examples, storage device 408 is used to store program instructions for execution by processing circuitry 402. Storage device 408, in one example, is used by software or applications 424 running on computing system 24 to temporarily store information during program execution.

Storage devices 408, in some examples, also include one or more computer-readable storage media. Storage devices 408 may be configured to store larger amounts of information than volatile memory. Storage devices 408 may further be configured for long-term storage of information. In some examples, storage devices 408 include non-volatile storage elements. Examples of such non-volatile storage elements include magnetic hard discs, optical discs, floppy discs, flash memories, or forms of electrically programmable memories (EPROM) or electrically erasable and programmable (EEPROM) memories. In some examples, storage devices 408 may store patient data, such as cardiac EGM strips.

Computing system 24, in some examples, also includes communication circuitry 406. Computing system 24, in one example, utilizes communication circuitry 406 to communicate with external devices, such as medical device 16 and EMR database 66 of FIG. 1. Communication circuitry 406 may include a network interface card, such as an Ethernet card, an optical transceiver, a radio frequency transceiver, or any other type of device that can send and receive information. Other examples of such network interfaces may include 3G, 4G, 5G, and WI-FI™ radios.

Computing system 24, in one example, also includes one or more user interface devices 410. User interface devices 410, in some examples, are configured to receive input from a user through tactile, audio, or video feedback. Examples of user interface devices(s) 410 include a presence-sensitive display, a mouse, a keyboard, a voice responsive system, video camera, microphone or any other type of device for detecting a command from a user. In some examples, a presence-sensitive display includes a touch-sensitive screen.

One or more output devices 412 may also be included in computing system 24. Output device 412, in some examples, is configured to provide output to a user using tactile, audio, or video stimuli. Output device 412, in one example, includes a presence-sensitive display, a sound card, a video graphics adapter card, or any other type of device for converting a signal into an appropriate form understandable to humans or machines. In some examples, output device(s) 412 include a display device. Additional examples of output device 412 include a speaker, a cathode ray tube (CRT) monitor, a liquid crystal display (LCD), or any other type of device that can generate intelligible output to a user.

Computing system 24 may include operating system 416. Operating system 416, in some examples, controls the operation of components of computing system 24. For example, operating system 416, in one example, facilitates the communication of one or more applications 424 and monitoring system 450 with processing circuitry 402, communication circuitry 406, storage device(s) 408, input device 404, user interface devices 410, and output device 412.

Application 422 may also include program instructions and/or data that are executable by computing system 24. Example application(s) 422 executable by computing system 24 may include monitoring system 450. Other additional applications not shown may alternatively or additionally be included to provide other functionality described herein and are not depicted for the sake of simplicity.

In accordance with the techniques of the disclosure, applications 424 include a monitoring system 450. Monitoring system 450 may be configured to receive patient data, evaluate the patient data, and generate output data. For instance, in one example, monitoring system 450 may generate notifications when monitoring system 450 determines that it is likely that patient 14 (FIG. 1) has experienced one or more cardiac arrhythmia events that belong to one or more types of cardiac arrhythmias. In another example, monitoring system 450 may generate one or more charts showing changes to one or more aspects of the cardiac rhythm of patient 14.

As shown in the example of FIG. 4, monitoring system 450 may, in some examples, implement an AI system 451 that includes a preprocessing unit 452 and a deep learning model 454. Although the remainder of this disclosure refers to preprocessing unit 452 and deep learning model 454, such references may apply equally to preprocessing units and deep learning models implemented in devices or systems other than computing system 24, such as in medical device 16 or external device 27 or a combination thereof. Moreover, AI system 451, preprocessing unit 452 and deep learning model 454 may be implemented outside the context of a monitoring system. Preprocessing unit 452 may preprocess input data, including cardiac EGM strips, that AI system 451 provides as input to deep learning model 454.

In some examples, deep learning model 454 is implemented using one or more neural network systems, deep learning systems, or other types of supervised or unsupervised machine learning systems. For example, deep learning model 454 may be implemented by a feedforward neural network, such as a convolutional neural network, a radial basis function neural network, a recurrent neural network, a modular or associative neural network. In some examples, AI system 451 trains deep learning model 454 with patient data, including cardiac EGM strips, for one or more populations of patients to generate data regarding one or more aspects of a cardiac rhythm of the patients in the populations. In some examples, after AI system 451 has pre-trained deep learning model 454, AI system 451 may further train deep learning model 454 with patient data specific to patient 14 or a smaller cohort of patients.

In some examples, AI system 451 trains deep learning model 454 with the patient data for a population of patients, determines an error rate of deep learning model 454, and then feeds the error rate back to deep learning model 454 so as to allow deep learning model 454 to update its predictions based on the error rate. In some examples, the error rate may correspond to differences between output data determined by deep learning model 454 based on input data and prelabeled output data for the same input data. In some examples, AI system 451 may use an error function to determine the error rate. The error function may be implemented using signal processing techniques and heuristics in the manner conventionally used to detect occurrences of cardiac arrhythmias. In some examples, monitoring system 450 may receive, from a user (e.g., patient 14, a clinician, or another type of person) feedback indicating whether a detected cardiac arrhythmia occurred in patient 14 within a particular time period. In some examples, monitoring system 450 may receive, from medical device 16, a message indicating that medical device 16 has detected (or has not detected) an occurrence of a cardiac arrhythmia in patient 14. In some examples, monitoring system 450 may obtain the feedback in other ways, such as by periodically checking the EMR data to determine if a cardiac arrhythmia occurred. Monitoring system 450 may update deep learning model 454 with the feedback. Thus, the training process may occur iteratively so as to incrementally improve the data generated by deep learning model 454 by "learning" from correct and incorrect data generated by deep learning model 454 in the past. Further, the training process may be used to further fine-tune deep learning model 454 that is trained using population-based data to generate more accurate data for a particular individual. In some examples, personnel of a monitoring service may provide the feedback.

In some examples, deep learning model 454 is implemented using a neural network. The neural network may include an input layer, and output layer, and one or more hidden layers between the input layer and the output layer. Each layer of the neural network may include one or more artificial neurons, which this disclosure refers to simply as neurons. The input layer of the neural network includes a plurality of input neurons. The input layer may include a separate input neuron for each sample value of a segment of a cardiac EGM strip. In some examples, the segment may be coterminous with the cardiac EGM strip. In other examples, the segment may be a subsegment of the cardiac EGM strip. For instance, in an example where the cardiac EGM strip comprises samples representing 45 seconds of a cardiac rhythm of patient 14, the segment may comprise samples representing the first 10 seconds of the cardiac EGM strip.

AI system 451 may provide overlapping segments of cardiac EGM strips to deep learning model 454. For example, AI system 451 may provide a segment comprising samples representing seconds 0 through 10 of a cardiac EGM strip, then provide a segment comprising samples representing seconds 5 through 15 of the cardiac EGM strip, then provide a segment comprising samples representing seconds 10 through 20 of the cardiac EGM strip, and so on. In some examples, computing system 24 may provide a segment that spans two or more cardiac EGM strips. For ease of explanation, application of a deep learning model to a cardiac EGM strip may in fact refer to application of the deep learning model to a segment of the cardiac EGM strip.

In some examples, deep learning model 454 comprises a convolutional neural network (CNN). For instance, in one example, a convolutional layer may follow an input layer of the type described above. A first convolutional layer neuron may receive input from a first set of input layer neurons consisting of a given number of consecutive input layer neurons; a second convolutional layer neuron may receive input from a second set of input layer neurons consisting of the same given number of consecutive input layer neurons, but offset from the first input layer neuron of the first set of input layer neurons by a stride length; a third convolutional layer neuron may receive input from a third set of input layer neurons consisting of the same given number of consecutive input layer neurons, but offset from the first input layer neuron of the second set of input layer neurons by the stride length; and so on. The given number of consecutive input neurons and the stride length are different hyperparameters of the CNN. One or more fully connected hidden layers may follow the convolutional layer.

In some examples of this disclosure, for each respective cardiac arrhythmia of a set of one or more cardiac arrhythmias, deep learning model 454 may generate data that indicate whether one or more occurrences of the respective cardiac arrhythmia are represented in a segment of a cardiac EGM strip. For instance, in one example, a hidden layer of deep learning model 454 provides input data to the output layer of deep learning model 454. For each respective cardiac arrhythmia of the set of cardiac arrhythmias, the output layer of deep learning model 454 that includes a separate output neuron corresponding to the respective cardiac arrhythmia. The output neuron corresponding to the respective cardiac arrhythmia receives input data from a single neuron in the hidden layer of deep learning model 454 that also corresponds to the respective cardiac arrhythmia type. The data generated by the hidden layer neuron corresponding to the respective cardiac arrhythmia comprises a probability value indicating a probability that an occurrence of the cardiac arrhythmia has happened in the segment of the cardiac EGM strip. An activation function of the output neurons may apply a thresholding function to the probability values generated by the hidden layer neurons. For each output neuron, the thresholding function may cause the output neuron to generate a first value (e.g., 1) if the probability value provided to the output neuron is greater than a threshold and to generate a second value (e.g., 0) if the probability value provided to the output neuron is less than the same threshold.

Furthermore, in the example of the previous paragraph, AI system 451 may use the probability values generated by the hidden layer to track where occurrences of cardiac arrhythmias happen within a cardiac EGM strip. For instance, as mentioned above, a cardiac EGM strip may be subdivided into segments and AI system 451 provides the segments to deep learning model 454 as input. Thus, by determining which segment of the cardiac EGM strip resulted in a highest probability values corresponding to a cardiac arrhythmia, AI system 451 may determine which segment most likely represents the occurrence of the cardiac arrhythmia.

As noted elsewhere in this disclosure, the input provided to deep learning model 454 may include patient data in addition to segments of cardiac EGM strips. For instance, in some examples, the patient data may additionally include data regarding the patient's physiological status (e.g., patient physiological statuses such as activity, posture, respiration, etc.), which may also be captured by medical device 16. Patient data corresponding to different physiological conditions (e.g., rest, resting at night, resting at night with high posture angle etc.) can be used as additional parameters for model training or input data for deep learning model 454. Using such data may enable AI system 450 to detect occurrences of cardiac arrhythmias during other disease conditions (e.g., a sensitive model for tachycardia during rest can be used to monitor heart failure (HF) patients; a model for bradycardia during activity can be used to monitor patients for chronotropic incompetence). In some examples, monitoring system 450 receives, via communication circuitry 406, EMR data for patient 14 from EMR database 66. In some examples, the EMR data stored by EMR database 66 may include many different types of historical medical information about patient 14. For example, EMR database 66 may store a medication history of the patient, a surgical procedure history of the patient, a hospitalization history of the patient, potassium levels of the patient over time, or one or more lab test results for the patient, etc. The EMR data may form part of the patient data used as input to deep learning model 454.

In some examples, deep learning model 454 converts the patient data into one or more vectors and tensors (e.g., multi-dimensional arrays) that represent the patient data. Deep learning model 454 may apply mathematical operations to the one or more vectors and tensors to generate a mathematical representation of the patient data. Deep learning model 454 may determine different weights that correspond to identified relationships between the patient data and the occurrence of cardiac arrhythmias. Deep learning model 454 may apply the different weights to the patient data to generate the probability values.

Figure 5:
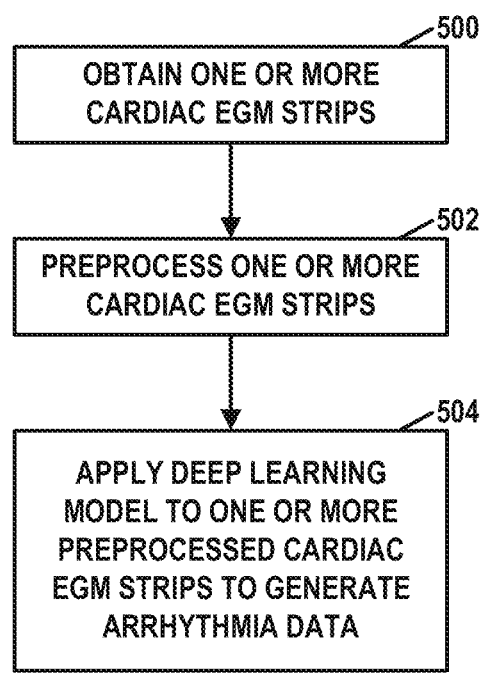
FIG. 5 is a flowchart illustrating an example operation of an artificial intelligence (AI) system in accordance with one or more techniques of the disclosure.

FIG. 5 is a flowchart illustrating an example operation in accordance with the techniques of the disclosure. For convenience, FIG. 5 is described with respect to FIG. 1 and FIG. 4. The flowcharts of this disclosure are presented as examples. Other examples in accordance with techniques of this disclosure may include more, fewer, or different actions, or actions may be performed in different orders or in parallel. The operation of FIG. 5 may be performed by an AI system implemented on one or more of medical device 16, computing system 24, external device 27, and/or other devices.

In the example of FIG. 5, the AI system may obtain one or more cardiac EGM strips for patient 14 (i.e., a current patient) (500). The AI system may obtain the one or more cardiac EGM strips for the patient 14 in one or more of various ways. For instance, in an example where computing system 24 implements the AI system, computing system 24 may obtain the one or more cardiac EGM strips for patient 14 from medical device 16 (e.g., by way of external device 27 and network 25). In some examples where the AI system is implemented in medical device 16, the AI system may obtain the one or more cardiac EGM strips by generating the one or more cardiac EGM strips based on data from electrodes. In some examples, the AI system may obtain the one or more cardiac EGM strips for the current patient from a database (e.g., EMR database 66) that stores the one or more cardiac EGM strips for the current patient. Other examples of obtaining cardiac EGM strips are described elsewhere in this disclosure.

Figure 15:
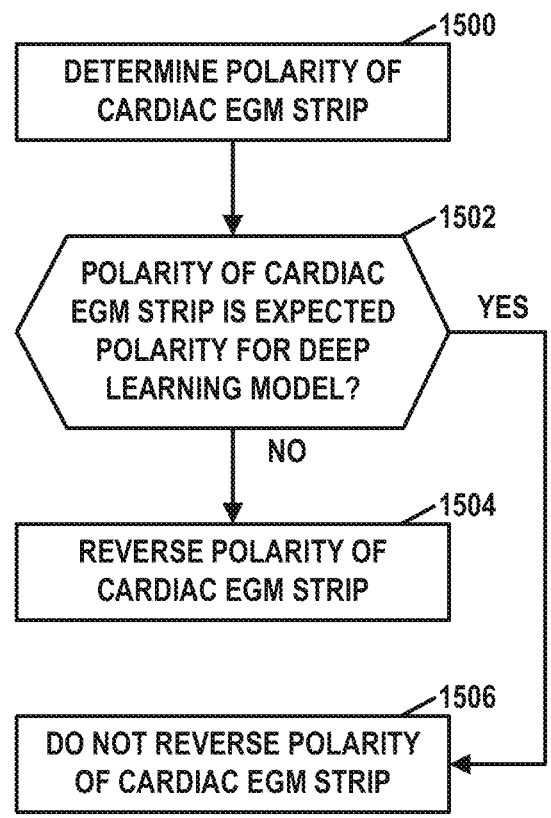
FIG. 15 is a flowchart illustrating a fifth example operation for preprocessing a cardiac EGM strip in accordance with one or more techniques of this disclosure.

Furthermore, in the example of FIG. 5, preprocessing unit 452 may preprocess the one or more cardiac EGM strips (502). Preprocessing unit 452 may preprocess the one or more cardiac EGM strips in one or more of various ways. For instance, FIGS. 6, 7, 9, 11, and 15 illustrate example ways of preprocessing the one or more cardiac EGM strips. In some examples, deep learning model 454 may be trained using cardiac EGM strips having certain characteristics, such as signal polarity, signal amplitude levels and changes, hardware characteristics, and so on. In such examples, after training, preprocessing unit 452 may preprocess one or more cardiac EGM strips such that the one or more cardiac EGM strips have the characteristics of the training cardiac EGM strips. This may allow deep learning model 454 to be used with cardiac EGM strips generated by more types of medical devices. For instance, as described in detail below, FIG. 7 and FIG. 15 are examples in which preprocessing unit 452 preprocesses the one or more cardiac EGM strips to conform to one or more characteristics of cardiac EGM strips on which deep learning model 454 was trained. Furthermore, in some examples, deep learning model 452 may be trained using preprocessed cardiac EGM strips generated by preprocessing unit 452. For instance, in the examples of FIG. 6, FIG. 7, FIG. 9, and FIG. 15, the AI system may train deep learning model 454 using preprocessed cardiac EGM strips.

After preprocessing unit 452 preprocesses the one or more cardiac EGM strips, the AI system may apply deep learning model 454 to the one or more preprocessed cardiac EGM strips to generate arrhythmia data indicating whether the one or more cardiac EGM strips represent one or more occurrences of one or more cardiac arrhythmias (504). That is, the input to deep learning model 454 may include the one or more preprocessed cardiac EGM strips or segments thereof. Deep learning model 454 may be trained according to any of the examples described elsewhere in this disclosure. When the AI system applies the deep learning model 454 to the one or more preprocessed cardiac EGM strips, the AI system may perform a feedforward pass through neurons of a neural network of deep learning model 454. The arrhythmia data may be output of the neural network.

Furthermore, in some examples, the AI system may generate output data based on the arrhythmia data. For example, the AI system may generate a table indicating times and types of detected occurrences of the cardiac arrhythmias. The times may be determined based on a timestamp provided by medical device 16 with cardiac EGM strips. In another example, the AI system may generate a chart showing the rate at which patient 14 is experiencing occurrences of a cardiac arrhythmia over time. The AI system may present the output data to one or more types of users. For example, the AI system may present the output data to patient 14, a healthcare provider of patient 14, a user at a healthcare monitoring organization, or another type of person.

Figure 6:
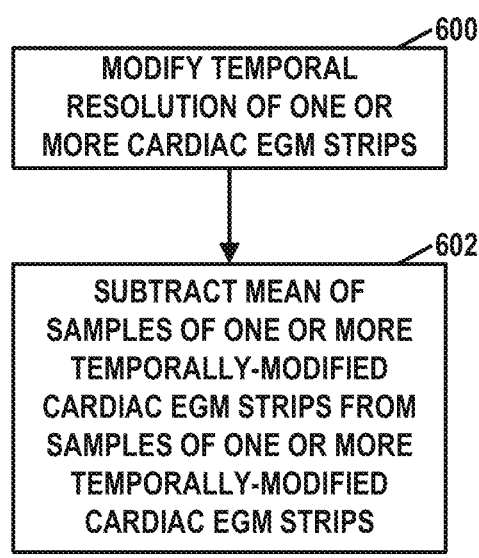
FIG. 6 is a flowchart illustrating a first example operation for preprocessing one or more cardiac electrogram (EGM) strips, in accordance with one or more techniques of this disclosure.
Figure 7:
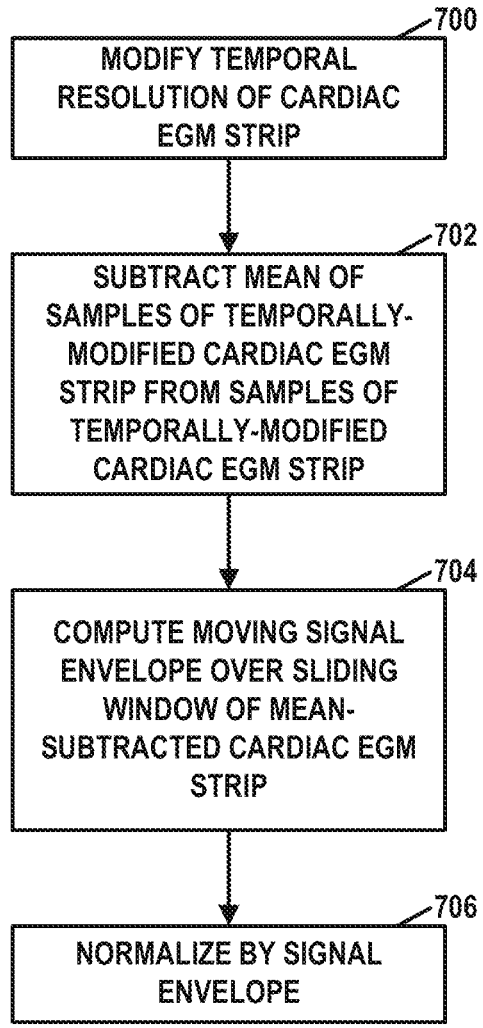
FIG. 7 is a flowchart illustrating a second example operation for preprocessing a cardiac EGM strip, in accordance with one or more techniques of this disclosure.

FIG. 6 is a flowchart illustrating a first example operation for preprocessing one or more cardiac EGM strips, in accordance with one or more techniques of this disclosure. In the example of FIG. 6, preprocessing unit 452 may generate one or more temporally-modified cardiac EGM strips by modifying a temporal resolution of the one or more cardiac EGM strips to match an expected temporal resolution of a deep learning model (602). For example, preprocessing unit 452 may modify the temporal resolution of the one or more cardiac EGM strips from 128 samples/second to 200 samples/second. Preprocessing unit 452 may modify the one or more cardiac EGM strips in one of various ways. For instance, in an example where the expected temporal resolution of the deep learning model is greater than the temporal resolution of the one or more cardiac EGM strips, preprocessing unit 452 may interpolate samples between samples of the one or more cardiac EGM strips. In an example where the expected temporal resolution of the deep learning model is less than the temporal resolution of the one or more cardiac EGM strips, preprocessing unit 452 may decimate samples in the one or more cardiac EGM strips. Other techniques of modifying the temporal resolution of the one or more cardiac EGM strips are possible.

Additionally, preprocessing unit 452 may generate one or more preprocessed cardiac EGM strips by subtracting a mean of samples of the one or more temporally-modified cardiac EGM strips from the samples of the one or more temporally-modified cardiac EGM strips (604). For instance, preprocessing unit 452 may determine the mean of the sample of the one or more temporally-modified cardiac EGM strips and then subtract that mean from each of the samples of the one or more temporally-modified cardiac EGM strips. In another example, preprocessing unit 452 may subtract the mean of samples of the one or more original cardiac EGM strips from the one or more original cardiac EGM strips and then modify the temporal resolution of the one or more resulting cardiac EGM strips, thus reversing the order of actions 600 and 602.

FIG. 7 is a flowchart illustrating a second example operation for preprocessing a cardiac EGM strip, in accordance with one or more techniques of this disclosure. Medical devices can be used in patients with varying physiological conditions (e.g., amount of fat/muscle) or underlying cardiac conditions. As a result, the signal levels in cardiac EGM strips can vary. There may also be amplitude changes in the signal levels in cardiac EGM strips for the same patient, e.g., due to posture changes or premature ventricular contractions (PVCs). Because there can be insufficient training data with such conditions either to train deep learning model 454 from scratch, or for transfer learning (e.g., a deep-learning model developed with external/resting Holter monitor applied to cardiac EGM strips from implanted monitors in active patients), applying additional normalization to the mean-removed waveform can improve the deep-learning model's arrhythmia and QRS detection performance.

Accordingly, in the example of FIG. 7, preprocessing unit 452 may generate one or more temporally-modified cardiac EGM strips by modifying a temporal resolution of the one or more cardiac EGM strips to match an expected temporal resolution of the deep learning model (700). Additionally, preprocessing unit 452 may generate one or more mean-subtracted cardiac EGM strips by subtracting a mean of samples of the one or more temporally-modified cardiac EGM strips from the samples of the one or more temporally-modified cardiac EGM strips (702). Preprocessing unit 452 may perform actions 700 and 702 in the same manner as described with respect to actions 600 and 602 of FIG. 6.

Furthermore, in the example of FIG. 7, to normalize for changing amplitude levels, preprocessing unit 452 may compute a moving signal envelope over a sliding window of the one or more mean-subtracted cardiac EGM strips (704). The sliding window may be 0.5 seconds in duration, 1-second in duration, 1.5 seconds in duration, or have another duration. In some examples, the envelope can be the standard deviation of the waveform samples in the moving window or the $99^{th}$ and $1^{st}$ percentile of the waveform samples in the moving window, or the maximum and minimum of the waveform samples in the moving window.

Figure 8A:
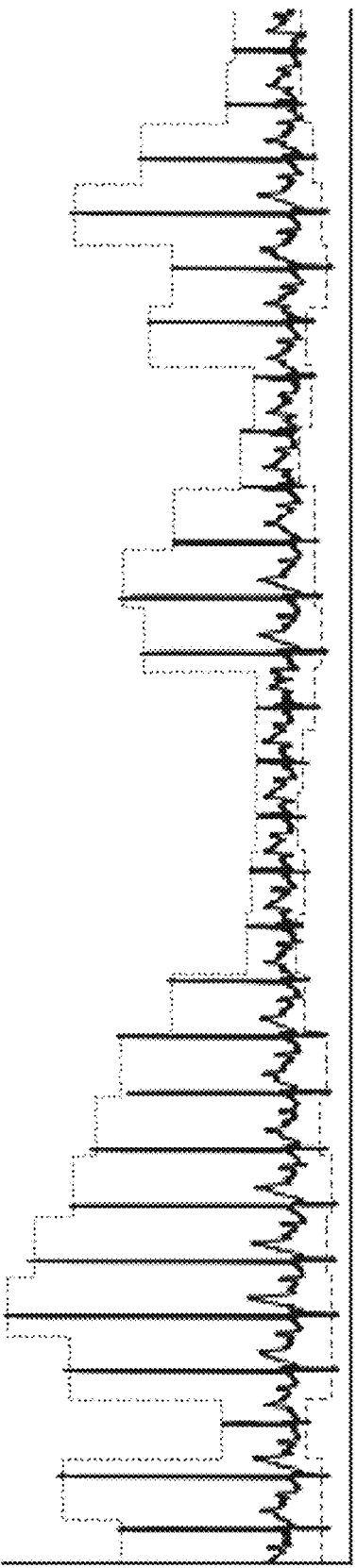
FIG. 8A is a conceptual diagram illustrating an example waveform and envelope determined in accordance with one or more techniques of this disclosure.

FIG. 8A is a conceptual diagram illustrating an example waveform and envelope determined in accordance with one or more techniques of this disclosure. In particular, FIG. 8A shows an example of the waveform (solid line) and the envelope computed over a 1-second moving window with the $99^{th}$ (upper dotted line) and $1^{st}$ (lower dashed line) percentile of samples in the moving window.

Figure 8B:
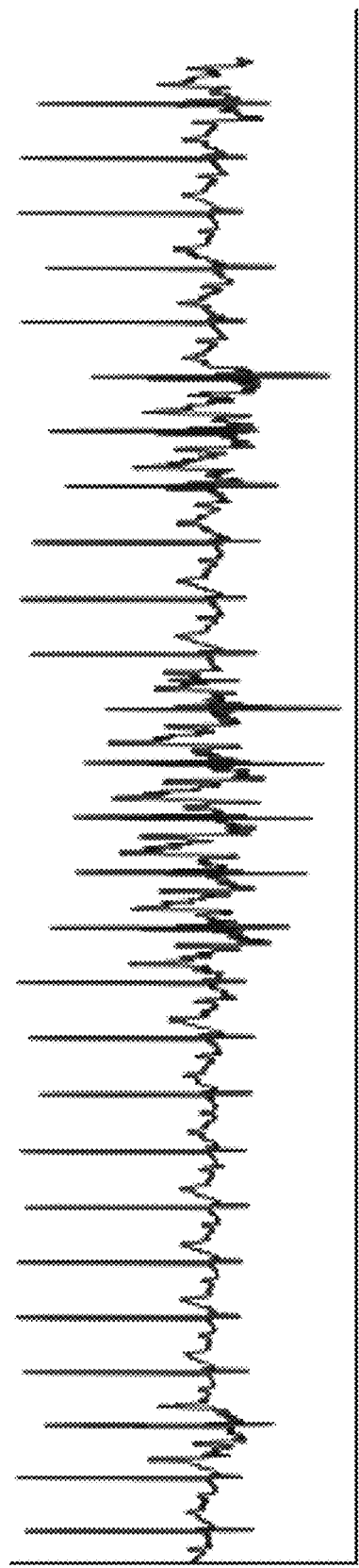
FIG. 8B is a conceptual diagram illustrating an example normalized waveform generated in accordance with one or more techniques of this disclosure.

Furthermore, in the example of FIG. 7, preprocessing unit 452 may normalize the mean-subtracted cardiac EGM strip based on the moving signal envelope (706). For instance, in one example, let d indicate the waveform, dU indicate the upper envelope and dL indicate the lower envelope (e.g., as shown in FIG. 8A). In this example, the normalized waveform may be computed sample-wise as d/(dU−dL). FIG. 8B is a conceptual diagram illustrating an example normalized waveform generated in accordance with one or more techniques of this disclosure. Notice in FIG. 8B that the waveform QRS-amplitude changes are minimized. In the example of FIG. 7, the AI system may provide the normalized mean-subtracted cardiac EGM strip as input to deep learning model 454.

In other examples, preprocessing unit 452 may perform additional preprocessing actions. For example, preprocessing unit 452 may normalize the entire waveform by its standard deviation, normalize the waveform by a constant gain factor, and/or perform other actions.

Figure 9:
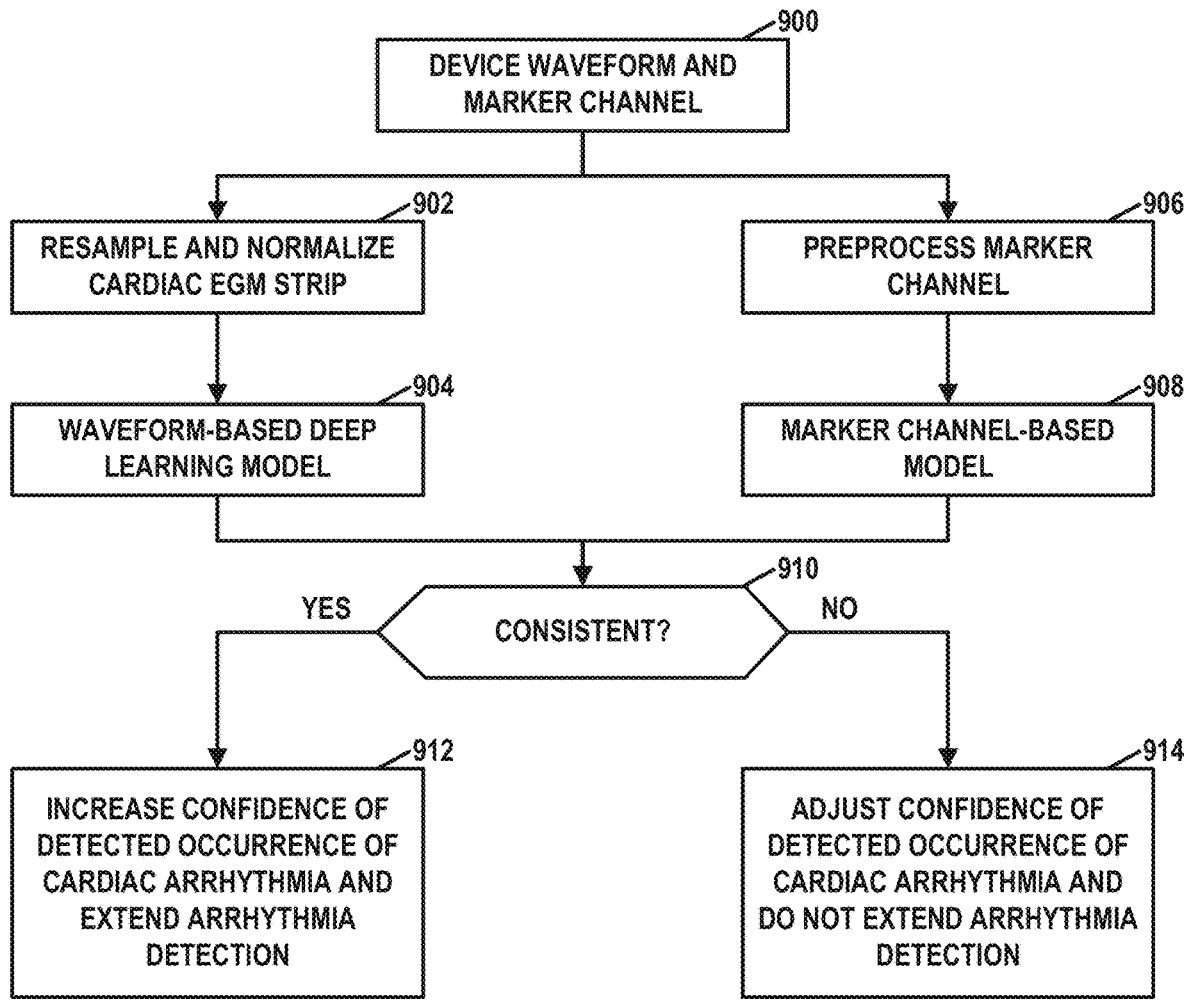
FIG. 9 is a flowchart illustrating an example operation of an AI system in accordance with one or more techniques of this disclosure.

FIG. 9 is a flowchart illustrating an example operation of an AI system in accordance with one or more techniques of this disclosure. The above-mentioned examples pertain to a deep learning model applied only on the cardiac EGM waveforms. Since some devices (e.g., medical device 16) have limited memory and battery power, the devices store and transmit a limited waveform segment. However, such devices may also generate and store additional marker channel information. The marker channel information may correspond to time periods during and before the time period to which the recorded cardiac EGM waveform corresponds. The marker channel information can provide additional arrhythmia diagnostics. For instance, in one example, the marker channel may indicate detected QRS complexes. Thus, in this example, the marker channel may comprise a series of samples that each indicate whether a QRS complex was detected during the time period corresponding to the sample. From this data, the R-R rate of the cardiac rhythm of patient 14 may be determined. The example of FIG. 9 pertains to using the marker channel for confirming and extending the arrhythmia detection of deep learning model 454.

As set forth in the example of FIG. 9, the AI system uses the marker channel for confirming and extending the arrhythmia detection of deep learning model 454. The waveform channel (e.g., a cardiac EGM strips) and marker channels may be processed by two separate models: A.) waveform-based deep learning model 454 and B.) a model based on the marker channel. If the arrhythmias detected by the two models agree during the duration of the waveforms, then the AI system increases the confidence of arrhythmia detection and extends the time-course of arrhythmia detection to beyond just the recorded waveform duration. In other words, the AI system may cause the device generating the waveform channel and the marker channel to continue generating the waveform channel. However, if the two models do not agree, the AI system may adjust the confidence of the arrhythmia detection (e.g., if the marker-based model has high reliability) but the time-course of the arrhythmia detection is not extended. In other words, the AI system may cause the device generating the waveform channel and the marker channel to stop generating the waveform channel. Not generating the waveform channel may reduce the power consumption of the device.

In the example of FIG. 9, the AI system may obtain one or more cardiac EGM strips and a marker channel (900). In some examples, the marker channel indicates detected QRS complexes in a cardiac rhythm of patient 14. Preprocessing unit 452 may resample and normalize the one or more cardiac EGM strips, e.g., as described with respect to FIG. 7 (902). Additionally, the AI system may apply deep learning model 454 (i.e., a waveform-based deep learning model) to the one or more preprocessed cardiac EGM strips to generate a first set of arrhythmia data (904). The AI system may apply the deep learning model 454 in the same way as described with respect to FIG. 5.

Furthermore, in the example of FIG. 9, preprocessing unit 452 may preprocess the marker channel (906). For example, preprocessing unit 452 may determine, based on the marker channel, R-R intervals, an average heart rate, one or more moving average heart rate trends, outlier-removal, a Lorenz plot based on the markers, heart rate variability, or other types of data. Additionally, preprocessing unit 452 may apply a marker channel-based deep learning model to the preprocessed marker channel to generate second arrhythmia data indicating a second set of occurrences of the one or more cardiac arrhythmias (908). In this example, the marker channel-based deep learning model may be implemented as a neural network that is trained to identify occurrences of cardiac arrhythmias in preprocessed marker channels.

In the example of FIG. 9, the AI system may determine whether the first set of arrhythmia data and the second set of arrhythmia data are consistent (910). For instance, the AI system may check whether there are any detected cardiac arrhythmia events that are not in the union of the first and second sets of arrhythmia data. Furthermore, the AI system may adjust a confidence level of an occurrence of one of the cardiac arrhythmias based on whether the occurrence of the cardiac arrhythmia is in both the first set of occurrences and the second set of occurrences or only in one of the first set of occurrences and the second set of occurrences. For instance, if the first set of arrhythmia data and the second set of arrhythmia data are consistent for a detected occurrence of the cardiac arrhythmia ("YES" branch of 910), the AI system may increase a confidence level of the detected occurrence of the cardiac arrhythmia and extend arrhythmia detection (912). For instance, the AI system may cause medical device 16 to continue generating cardiac EGM strips. On the other hand, if the first set of cardiac arrhythmia data and the second set of cardiac arrhythmia data are not consistent for a detected occurrence of the cardiac arrhythmia ("NO" branch of 910), the AI system may adjust the confidence level of the detected occurrence of the cardiac arrhythmia and does not extend arrhythmia detection (914). For instance, the AI system may cause medical device 16 to stop generating cardiac EGM strips. Thus, the AI system may perform one or more of adjusting a confidence level of an occurrence of one of the cardiac arrhythmias based on whether the occurrence of the cardiac arrhythmia is in both the first set of occurrences and the second set of occurrences or only in one of the first set of occurrences and the second set of occurrences, or extending, based on the occurrence of the cardiac arrhythmia being in both the first set of occurrences and the second set of occurrences, a duration of a monitoring session of a medical device that generates the one or more cardiac EGM strips.

The confidence level may be used in various ways. For example, monitoring system 450 may output the confidence level for display. In this example, display the confidence level may help a monitoring professional or healthcare professional determine how to act on information about the cardiac arrhythmias. In some examples, if the confidence level is below a predetermined threshold, monitoring system 450 does not present information about the cardiac arrhythmias to a user.

Furthermore, in some examples, medical device 16 generates a cardiac EGM strip of limited duration (e.g., 45 seconds) upon detecting a cardiac arrhythmia or an occurrence of a patient-trigger. Diagnostic devices have a patient trigger (e.g., a button on the device) which the patient can press upon feeling symptoms. These are considered symptomatic ECG episodes. Around the patient activation/trigger time, the device captures an extended waveform signal that is transmitted for review. Additionally, in such examples, medical device 16 generates a marker channel for a more extended duration (e.g., 5 minutes before and 5 minutes after detecting a cardiac arrhythmia or the occurrence of a patient-trigger. Consistent with the example of FIG. 9, the AI system may preprocess the cardiac EGM strip (902) and apply deep learning model 454 to the preprocessed cardiac EGM strip to generate arrhythmia data (904). Furthermore, in such examples, the AI system may apply a marker channel-based model to a portion of the marker channel markers that corresponds to a time before and during the time to which the cardiac EGM strip corresponds (908). In such examples, the AI system may determine whether the outputs of the waveform-based deep learning model 454 and the marker channel-based deep learning model are consistent. For example, the AI system may determine that the outputs of the waveform based deep learning model 454 are consistent with the outputs of the marker channel-based deep learning model if deep learning model 454 determines that a waveform of a cardiac EGM strip includes an occurrence of ventricular tachycardia and the marker-based deep learning model detects a high-rate episode with low RR-variability.

Based on whether or not the output of the two models is consistent, the AI system may adjust the overall arrhythmia occurrence likelihood in the waveform. For example, if there is consistency between the marker-channel based model and the waveform-based deep learning model 454 (e.g., the marker-channel detects tachyarrhythmia is greater than or equal to 120 beats per minute (BPM) in the duration of the recorded waveform, and the waveform-base deep learning model 45 detects ventricular tachycardia (VT)), monitoring system 450 may use the marker-channel's trend to present information about what occurred prior to the start of the cardiac arrhythmia detected in the cardiac EGM strip. For instance, monitoring system 450 may output a graph, such as that shown in FIG. 10B, that shows how the patient's heart behaved prior to the onset of the cardiac arrhythmia. This may help a physician diagnose a heart condition of patient 14.

In one example, medical device 16 may generate one or more cardiac EGM strips that represent a limited-duration waveform in response to an on-board detection algorithm determining that a cardiac arrhythmia is occurring. Medical device 16 may itself implement the on-board detection algorithm. In one example, the on-board detection algorithm may determine that a 45-second tachycardiac episode occurred from 10:30:00 AM to 10:30:45 AM. In this example, medical device 16 may provide one or more cardiac EGM strips representing the 45-second waveform to the AI system for cardiac arrhythmia reporting. Furthermore, in this example, the AI system may apply waveform-based deep learning model 454 to determine whether the one or more cardiac EGM strips contain any cardiac arrhythmias during the 45-second time period (i.e., from 10:30:00 AM to 10:30:45 AM). Monitoring system 450 may report any cardiac arrhythmias detected by deep learning model 454 based on the one or more cardiac EGM strips. Additionally, in some examples, medical device 16 may generate a marker channel that covers a longer duration (e.g., from 10:20:00 AM to 10:35:00 AM). Medical device 16 may also provide this marker channel to the AI system for cardiac arrhythmia reporting. A marker channel-based model of the AI system may use the marker channel to detect arrhythmias in the time periods during and adjacent to the time period corresponding to the one or more cardiac EGM strips (e.g., 10:29:00 AM to 10:31:00 AM). If the cardiac arrhythmias detected by the marker channel-based model are consistent with the cardiac arrhythmias detected by the waveform-based deep learning model 454 in the time periods during and adjacent to the time period corresponding to the one or more cardiac EGM strips, monitoring system 450 may output an indication of the cardiac arrhythmias detected by the waveform-based deep learning model 454 based on the one or more cardiac EGM strips for the time period 10:30:00 AM to 10:30:45 AM. Additionally, monitoring system 450 may output additional information from the marker channel (from 10:20:00 AM to 10:35:00 AM), such as the average HR and HR variability trend before, during, and after the recorded waveform duration. In this way, monitoring system 450 may output information that provides a physician with additional cardiac arrhythmia-related information. For instance, the physician may be able to see whether there was a sudden-onset tachycardia.

In some examples, if medical device 16 implements both the waveform-based deep learning model 454 and the marker channel-based model, medical device 16 may determine whether there is consistency between the cardiac arrhythmias identified by the waveform-based deep learning model 454 and the marker channel-based model for a time period, medical device 16 may keep recording the waveform for a longer duration. If medical device 16 determines that there is no consistency, medical device 16 may stop recording/delete this waveform episode.

Figure 10A:
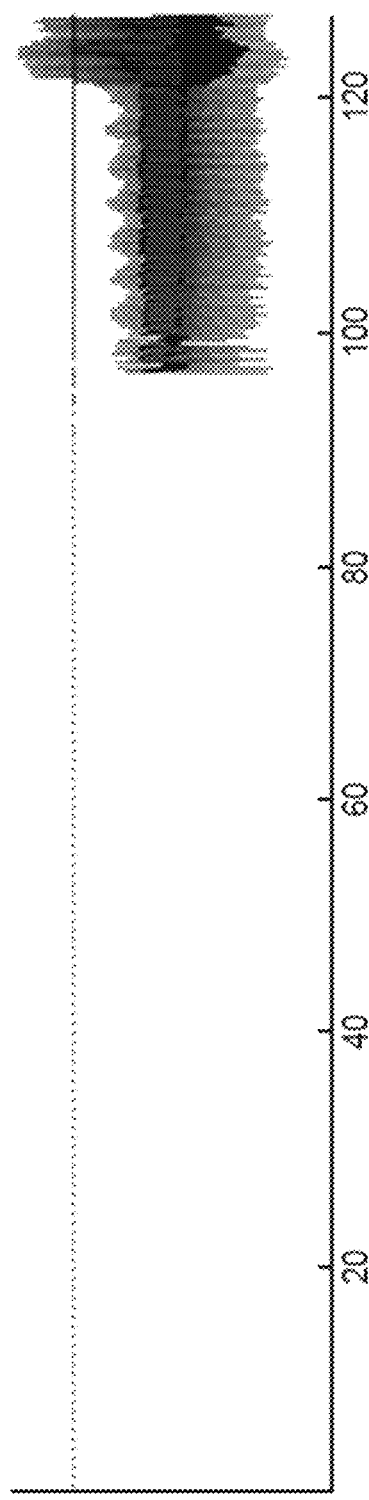
FIG. 10A is a conceptual diagram illustrating a chart of an example cardiac waveform and device-detected QRS markers.
Figure 10B:
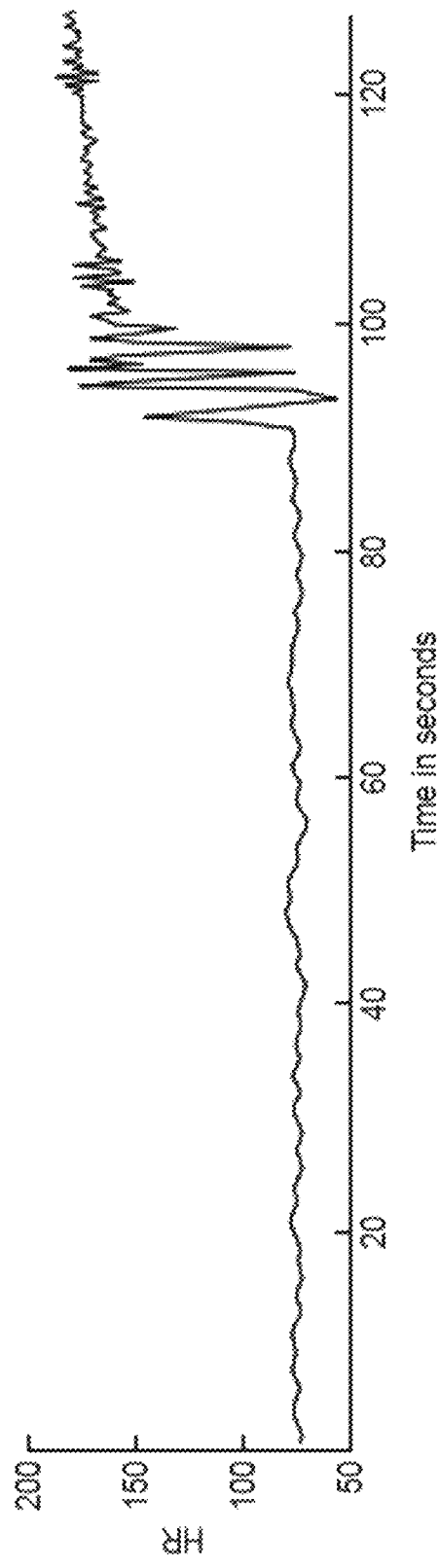
FIG. 10B is a conceptual diagram illustrating a chart of an example marker-channel-based heart rate over time.

FIG. 10A is a conceptual diagram illustrating a chart of an example cardiac waveform and device-detected QRS markers. FIG. 10B is a conceptual diagram illustrating a chart of an example marker-channel-based heart rate over time. FIG. 10A and FIG. 10B are for the same data and time-aligned on the x-axis. In the example of FIG. 10A, marker channel information is shown as a series of dots arranged in a horizontal line. The dark zigzagging line beginning around second 95 is a waveform represented by one or more cardiac EGM strips. In FIG. 10A, the markers are stored on medical device 16 from a time period much before the limited waveform segment. It may require fewer computational resources to generate and store the marker data than the cardiac EGM strips. As shown in the example of FIG. 13B, the waveform and marker channel-based deep learning models agree that the detection was a ventricular tachycardia (VT) occurred at ~130 second mark and the time course of arrhythmia detection is extended from just the 120-130 seconds segment (within the duration of the waveform) to ~2 minutes before arrhythmia onset; this indicates a rapid increase in HR and a VT event.

While other examples described in this disclosure use deep-learning model 452 on preprocessed cardiac EGM strips directly, the AI system may, in other examples, perform deep-learning QRS and arrhythmia detection on a transformed signal (e.g., in frequency domain). For instance, in one example, neural networks can have several initial convolution layers to extract the low-level features of the input signal. In some examples, the AI system may learn the convolution kernel/filter parameters from the data directly. In some examples, to reduce computational complexity while maintaining performance, existing expert knowledge can be used to preprocess the data for the deep-learning. For example, as part of preprocessing the one or more cardiac EGM strips, the AI system may decompose the waveform represented by the one or more cardiac EGM strips into decomposed waveforms that correspond to different frequency bands. The different frequency bands may correspond to different aspects of an ECG signal, such as the high-frequency QRS signal, the lower-frequency P-wave signal, and so on. In this example, the AI system may generate arrhythmia data by applying deep-learning model 452 to the decomposed waveforms.

Figure 11:
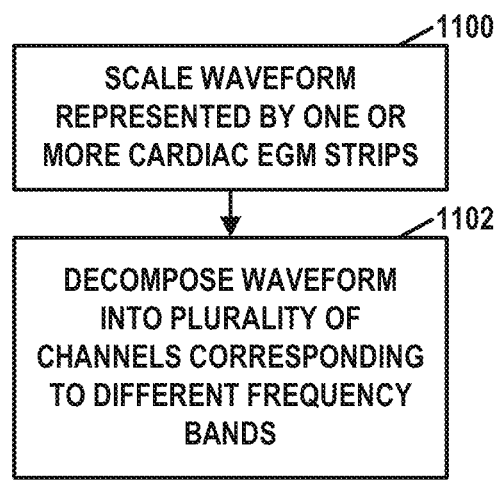
FIG. 11 is a flowchart illustrating a third example operation for preprocessing a cardiac EGM strip in accordance with one or more techniques of this disclosure.

FIG. 11 is a flowchart illustrating a third example operation for preprocessing a cardiac EGM strip in accordance with one or more techniques of this disclosure. In the example of FIG. 11, as part of preprocessing the one or more cardiac EGM strips, preprocessing unit 452 may scale the waveform represented by the one or more cardiac EGM strips (1100). The scaling in this example, and the other parts of the disclosure, may be to limit the range of EGM amplitude scales on which the model needs to be trained. Additionally, in the example of FIG. 11, preprocessing unit 452 may decompose the waveform represented by the one or more cardiac EGM strips into a plurality of channels corresponding to different frequency bands (1002). Subsequently, as part of applying deep learning model 454 to the segments of the preprocessed cardiac EGM strip, the AI system may apply the deep learning model to the channels to generate the arrhythmia data.

Figure 12:
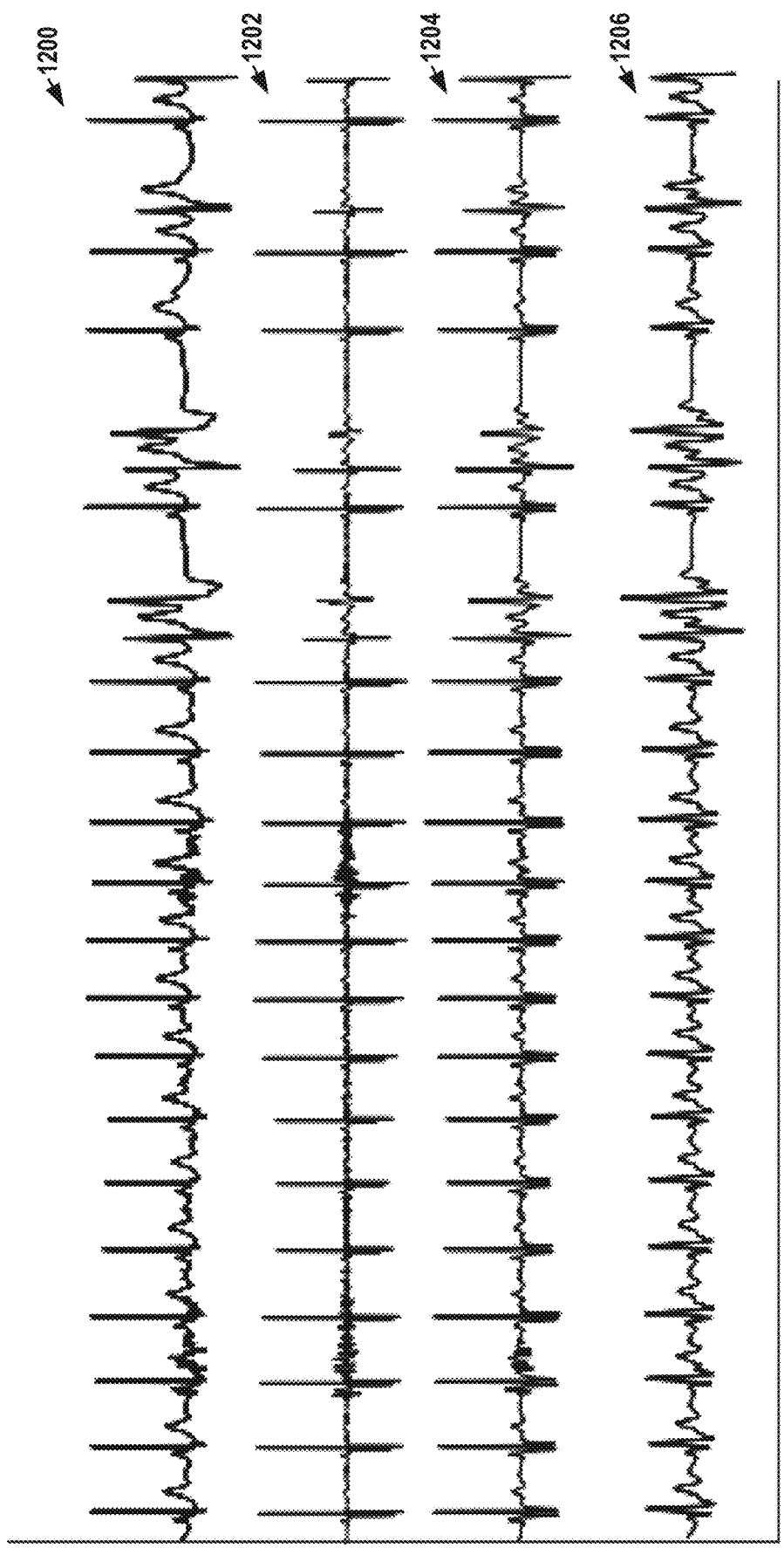
FIG. 12 is a conceptual diagram illustrating an example raw cardiac waveform and waveforms for channels corresponding to different frequency bands in accordance with one or more techniques of this disclosure.

Thus, in the example of FIG. 11, after the waveform scaling, the signal is decomposed into multiple channels with each channel corresponding to a different frequency band. FIG. 12 is a conceptual diagram illustrating an example raw cardiac waveform and waveforms for channels corresponding to different frequency bands in accordance with one or more techniques of this disclosure. FIG. 12 shows an example where instead of the raw waveform 1200 being used for deep-learning, 3 channels (1202, 1204, and 1206) derived from the raw waveform 1200 using (i) stationary wavelet decomposition and (ii) band-specific time-delays for QRS alignment are used. Notice that channel 1202 consists of mainly high-frequency features (typically corresponding to the QRS segment) and band 1206 consists of lower-frequency features (e.g., p-wave). Thus, instead of having a 1×N vector as input to deep-learning model 454, the 3×N matrix (with the stationary wavelet-decomposed and aligned signals) is the input. Having pre-processed signals can help speed up learning and/or decrease complexity of deep learning model 454.

Figure 13:
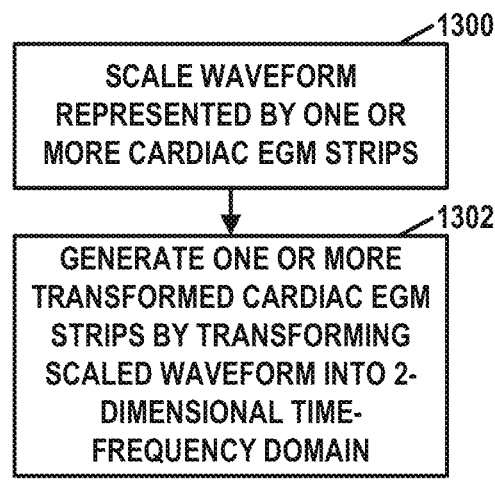
FIG. 13 is a flowchart illustrating a fourth example operation for preprocessing a cardiac EGM strip in accordance with one or more techniques of this disclosure.

FIG. 13 is a flowchart illustrating a fourth example operation for preprocessing a cardiac EGM strip in accordance with one or more techniques of this disclosure. In the example of FIG. 13, as part of preprocessing the one or more cardiac EGM strips, preprocessing unit 452 may scale the waveform represented by the one or more cardiac EGM strips (1300). Preprocessing unit 452 may scale the waveform in accordance with any of the examples provided in above with respect to FIG. 11.

Furthermore, in the example of FIG. 13, preprocessing unit 452 may generate one or more transformed cardiac EGM strips by transforming the scaled waveform into a 2-dimensional time-frequency domain (1302). For instance, preprocessing unit 452 may transform the scaled waveform into a spectrogram. Subsequently, the AI system may apply deep learning model 454 to the one or more preprocessed cardiac EGM strips by applying the deep learning model to the one or more transformed cardiac EGM strips. Monitoring system 450 may output an image of the spectrogram for display. Furthermore, in some examples, deep learning model 454 may be implemented in a manner similar to image recognition deep learning models. For instance, deep learning model 454 may comprise convolutional layers that apply various filters to the spectrogram. Furthermore, in some examples, by presenting the whole spectrogram to deep learning model 454, the AI system may enable deep learning model 454 to determine an optimal set of frequencies and features for this set of signals.

Figure 14:
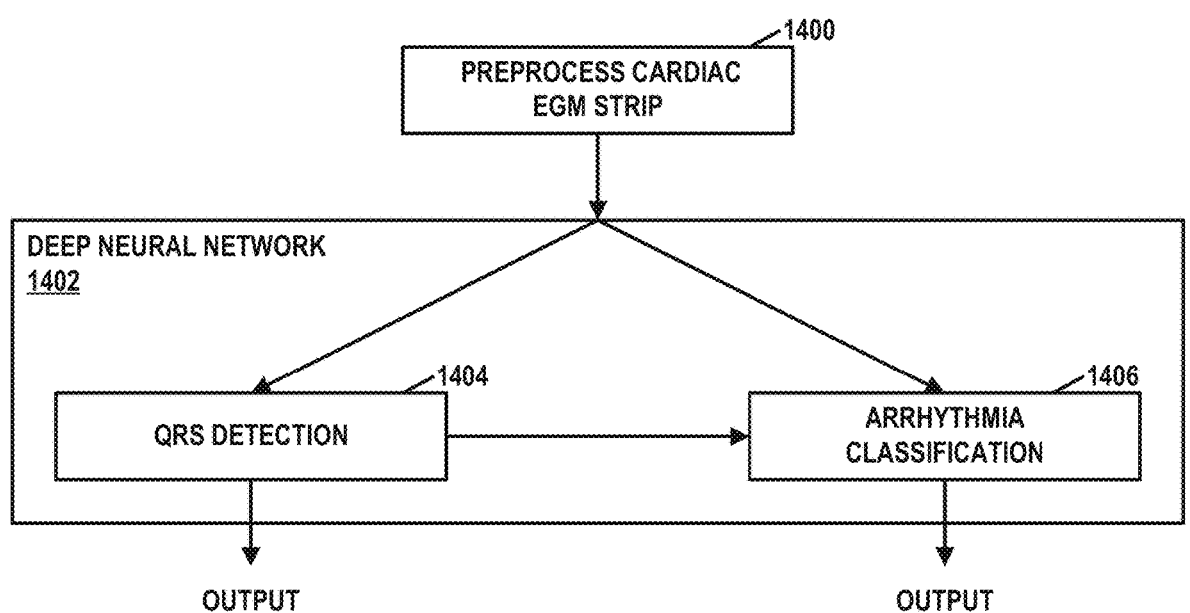
FIG. 14 is a flowchart illustrating an example operation of an AI system in accordance with one or more techniques of this disclosure.

FIG. 14 is a conceptual diagram illustrating an example operation of an AI system in accordance with one or more techniques of this disclosure. In the example of FIG. 14, preprocessing unit 452 may preprocess the cardiac EGM strip (1400). For instance, in the example of FIG. 14, preprocessing unit 452 may apply a learned scaling factor to the waveform represented by the cardiac EGM strip. In some examples, the AI system may learn the scaling factor by repeatedly testing different scaling factors with training data and determining which scaling factors result have the best performance in correctly detecting cardiac arrhythmias.

The AI system may provide the preprocessed cardiac EGM strip as input to a deep neural network 1402. Deep neural network 1402 may be part of deep learning model 454.

In the example of FIG. 14, as part of applying deep learning model 454, the AI system may perform QRS detection (1402). As part of performing QRS detection, deep neural network 1402 may determine QRS probability values corresponding to a plurality of time points. Each of the QRS probability values indicates a respective probability that a peak of a QRS complex occurs during the time point corresponding to the QRS probability value. For instance, an initial set of layers of the deep neural network may determine the QRS probability values based on the preprocessed EGM strip.

In addition, deep neural network 1402 may perform arrhythmia classification (1406) based on the preprocessed cardiac EGM strip and the QRS probability values. That is, deep neural network 1402 may detect a set of occurrences of the one or more cardiac arrhythmias by providing the QRS probability values and the preprocessed cardiac EGM strip as input to a neural network that generates arrhythmia data. Thus, in this step, the QRS probability values are combined with deeper layers of deep learning model 454 to detect cardiac arrhythmia events.

As shown in the example of FIG. 14, the AI system may separately output the QRS probability values and occurrence times and the arrhythmia data indicating whether and where the cardiac EGM strip represents one or more occurrences of one or more cardiac arrhythmias. This may provide the advantage of providing two separate paths for QRS and arrhythmia detection is interpretability, since ECG readers/technicians trained in the art typically use the QRS are a first step in arrhythmia determination. Furthermore, the 2-way interaction between the QRS and arrhythmia detection modules can help provide arrhythmia-specific QRS detection and enhanced QRS detection based on the detected occurrences of cardiac arrhythmias (e.g., if the QRS model flags PVCs/bigeminy but is not sure which, and if the arrhythmia model says its PVC, then the rhythm is bigeminy, else it is T-wave oversensing).

FIG. 15 is a flowchart illustrating a fifth example operation for preprocessing a cardiac EGM strip in accordance with one or more techniques of this disclosure. In this example of FIG. 15, the operation includes signal polarity and signal characteristics pre-processing in accordance with one or more techniques of this disclosure. In some examples, deep learning model 454 is trained with data from a certain type of hardware and cardiac EGM signal characteristics. For example, a user may want to use a large dataset to train deep learning model 454. The dataset may include waveform morphologies are "upright," but deep-learning model 454 may also need to be used with devices where the waveform morphologies are not always upright. For example, some devices generate cardiac EGM signals in which the R wave initially deflects in a negative direction and other devices may generate cardiac EGM signals in which the R wave initially deflects in a positive direction. To address such a scenario, deep-learning model 454 can be trained on the original set of waveforms and their polarity-reversed version, both of which have the same arrhythmia content. In cases where the AI system needs to use a pre-existing deep learning model (i.e., where re-training is not possible), the waveform signal can be transformed to meet the deep-learning input characteristics.

Thus, in the example of FIG. 15, the AI system may determine a polarity of the cardiac EGM strip (1500). The AI system may then determine whether the polarity of the cardiac EGM strip is the same as an expected polarity for deep learning model 454 (1502). In response to determining that the polarity of the cardiac EGM strip is not the expected polarity for deep learning model 454 ("NO" of 1502) the AI system may reverse the polarity of the cardiac EGM strip (1504). Otherwise, the AI system does not reverse the polarity of the cardiac EGM strip (1506).

The AI system may determine the polarity of the cardiac EGM strip in one of various ways. For instance, in one example, when medical device 16 is implanted in patient 14, an implanting physician may program a setting to indicate if the polarity is reversed. In this example, medical device 16 may include, in cardiac EGM strips generated by medical device 16, data indicating a polarity of the cardiac EGM strips generated by medical device 16.

In another example, when data, such as cardiac EGM strips, from medical device 16 are viewed and analyzed at a monitoring center, a monitoring center technician can flag the data if the waveform morphology is reversed for patient 14. For short-medium term monitoring, such flagging may only need to be done at the start of monitoring. For longer-term applications, such morphology flagging can be done periodically (e.g., every month) to account for any device drifts.

In another example of determining a polarity of the cardiac EGM strip, the AI system may use the P-wave and T-wave morphologies to estimate if the waveform morphology is flipped. That is, the P-wave and T-wave start and end a cardiac cycle always deflect in the same direction. Thus, based on the initial detection of the P-wave and the T-wave, the AI system may determine the polarity of the cardiac EGM strip.

In another example of determining a polarity of the cardiac EGM strip, the AI system may use a deep learning model to detect the waveform polarity as a pre-cursor to applying a deep learning model (e.g., deep learning model 454) for cardiac arrhythmia detection. Thus, in this example, deep learning model 454 may be considered to be a first deep learning model and the AI system may apply an additional deep learning model to the cardiac EGM strip to determine the polarity of the cardiac EGM strip. The additional deep learning model may comprise an artificial neural network that is trained to classify the polarities of cardiac EGM strips.

In a related example, the AI system may use a deep learning similarity model to check if the input signal morphology is similar to the signal morphology required for the arrhythmia detection model and performing an appropriate signal transformation. The deep learning similarity model may take multiple waveforms as input and may generate output data that indicate whether the waveforms are similar. The waveforms in this example may be waveforms represented by cardiac EGM strips. In this example, "similarity" may refer to same morphology/polarity here. In other words, the deep learning similarity model may compare waveforms of cardiac EGM strips from multiple devices to determine if the waveforms have a similar morphology. The deep learning similarity model may be implemented as a neural network.

The AI system may modify properties of a cardiac EGM strip in addition to or in the alternative to the polarity of the cardiac EGM strip. For example, the AI system may generate device classification data that indicates a class of the device that generated the cardiac EGM strip. Different classes of devices may have different hardware characteristics (e.g., bandwidth of the input signal). Accordingly, it may be advantageous to re-filter and/or transform the signal of the cardiac EGM strip to match the input characteristics of deep learning model 454 prior to applying the deep learning model to the cardiac EGM strip. For example, the AI system may filter the signal of the cardiac EGM strip to change a bandwidth of the signal. For instance, in this example, the AI system may scale the samples of the signal of the cardiac EGM strip such that the samples are distributed in an expected range of sample values for deep learning model 454. In some examples, as part of filtering the signal of the cardiac EGM strip to change the bandwidth of the signal, the AI system may increase or decrease the sample rate of the signal of the cardiac EGM strip to match an expected sample rate of deep learning model 454. The AI system may use interpolation to adjust the sample rate. Because of the different characteristics of different classes of devices, deep learning model 454 may not be able to correctly identify occurrences of cardiac arrhythmias in cardiac EGM strips generated by multiple types of devices.

Figure 16:
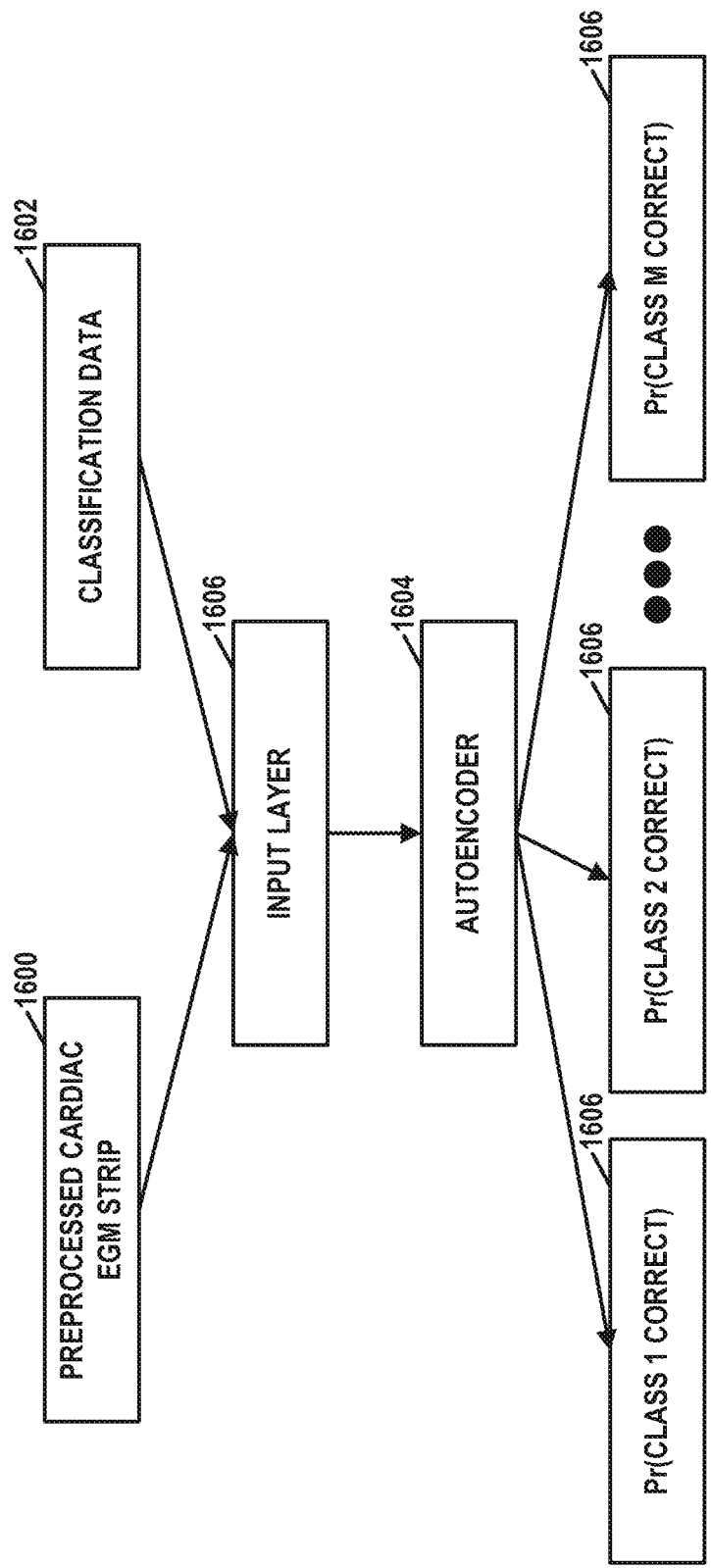
FIG. 16 is a conceptual diagram illustrating an example operation of an AI system that includes an autoencoder in accordance with one or more techniques of this disclosure.

FIG. 16 is a conceptual diagram illustrating an example operation of an AI system that includes an autoencoder in accordance with one or more techniques of this disclosure. In the example of FIG. 16, the AI system uses autoencoding to adjudicate device classifications. In other words, the AI system may use autoencoding to check whether the classification data assigned to a cardiac EGM strip is correct. The classification data assigned to a cardiac EGM strip may comprise data generated by another device (e.g., medical device 16) that indicates a cardiac arrhythmia detected in the cardiac EGM strip.

As shown in the example of FIG. 16, the input to the AI system may include one or more preprocessed cardiac EGM strips 1600 and classification data 1602. The preprocessed cardiac EGM strips 1600 represent waveforms of a cardiac rhythm of patient 14. The preprocessed cardiac EGM strips 1600 may be preprocessed in one or more of various ways, including in accordance with any of the examples provided elsewhere in this disclosure. Classification data 1602 may include data that indicate a class of cardiac arrhythmia detected in the cardiac EGM strip upon which preprocessed cardiac EGM strip 1600 is based. For example, classification data 1602 may indicate that medical device 16 determined that the cardiac EGM strip contains an occurrence of atrial fibrillation.

An autoencoder 1604 classifies the probability that classification data 1602 is correct. Autoencoder 1604 may be implemented as a deep neural network. The deep neural network of autoencoder 1604 comprises an input layer 1604, a set of hidden layers, and an output layer. Autoencoder 1604 is trained such that, when a preprocessed cardiac EGM strip and a set of classification data are provided as input to autoencoder 1604, the output layer outputs a recreated version of the preprocessed cardiac EGM strip. Autoencoder 1604 may be trained according to one of the various techniques for training autoencoders known in the art. For instance, the AI system may compare the recreated version of the preprocessed cardiac EGM strip to the original preprocessed cardiac EGM strip 1600 to determine error values that may be used in a backpropagation algorithm to update parameters of the deep neural network of autoencoder 1604. As shown in the example of FIG. 16, the AI system may provide one or more of preprocessed cardiac EGM strips 1600, or segments thereof, and device classification data 1602 to an input layer 1606 of the deep neural network of autoencoder 1604.

The output of one of the hidden layers of the deep neural network of autoencoder 1604 may generate probability values 1606. Each of the probability values corresponds to a different class of cardiac arrhythmia and indicates a level of confidence that classification data 1602 correctly identifies the classes of cardiac arrhythmias in the cardiac EGM strip. In some examples, to accelerate training of the deep neural network of autoencoder 1604, the layers up through the intermediate layer are pretrained separately from the subsequent layers of the deep neural network of autoencoder 1604.

Furthermore, in the example of FIG. 16, the AI system may use probability values 1606 to determine whether classification data 1602 correctly identifies cardiac arrhythmia in the cardiac EGM strip. For instance, the AI system may identify the highest one of probability values 1606 and compare the cardiac arrhythmia corresponding to the highest one of probability values 1606 to a cardiac arrhythmia indicated by classification data 1602 to determine whether classification data 1602 indicates the cardiac arrhythmia corresponding to the highest one of probability values 1606.

Figure 17:
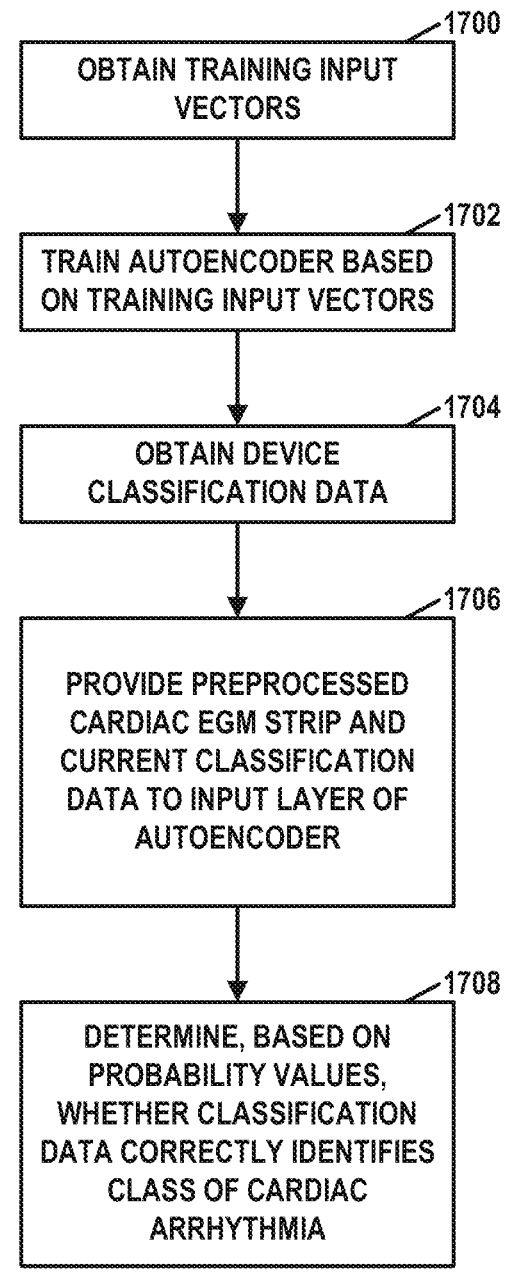
FIG. 17 is a flowchart illustrating an example operation in which an autoencoder is used to confirm device classifications in accordance with one or more techniques of this disclosure.

FIG. 17 is a flowchart illustrating an example operation in which an autoencoder is used to confirm device classifications in accordance with one or more techniques of this disclosure. As shown in the example of FIG. 17, and consistent with the example of FIG. 16, the AI system may obtain training input vectors (1700). Each of the training input vectors comprises a segment of a training cardiac EGM strip and device classification data that indicate one or more cardiac arrhythmias detected in the training cardiac EGM strip. The AI system may train autoencoder 1604 based on the training input vectors to reconstruct the training cardiac EGM strips of the training input vectors (1702).

Furthermore, in the example of FIG. 17, the AI system may obtain additional classification data (1704). For instance, in one example, the AI system may receive the additional classification data from a medical device, such as medical device 16.

The AI system may provide a segment of the preprocessed cardiac EGM strip and the classification data to input layer 1606 of autoencoder 1604 (1706). Furthermore, the AI system may determine, based on probability values generated by an intermediate layer of autoencoder 1604, whether the classification data correctly identifies cardiac arrhythmias, if any, in the preprocessed cardiac EGM strip (1708). Each of the probability values corresponds to a different cardiac arrhythmia and indicates a level of confidence that the preprocessed cardiac EGM strip contains the cardiac arrhythmia.

The following is a non-limiting set of examples that are in accordance with one or more techniques of this disclosure.

Example 1

A method comprising: obtaining, by a computing system, one or more cardiac electrogram (EGM) strips that represent a waveform of a cardiac rhythm of a patient; preprocessing, by the computing system, the one or more cardiac EGM strips; and applying, by the computing system, a deep learning model to the one or more preprocessed cardiac EGM strips to generate arrhythmia data indicating whether the one or more cardiac EGM strips represent one or more occurrences of one or more cardiac arrhythmias.

Example 2

The method of example 1, wherein preprocessing the one or more cardiac EGM strips comprises: generating, by the computing system, one or more temporally-modified cardiac EGM strips by modifying a temporal resolution of the one or more cardiac EGM strips to match an expected temporal resolution of a deep learning model; and generating, by the computing system, one or more preprocessed cardiac EGM strips by subtracting a mean of samples of the one or more temporally-modified cardiac EGM strips from the samples of the one or more temporally-modified cardiac EGM strips.

Example 3

The method of example 1, wherein preprocessing the one or more cardiac EGM strips comprises:
generating, by the computing system, one or more temporally-modified cardiac EGM strips by modifying a temporal resolution of the one or more cardiac EGM strips to match an expected temporal resolution of the deep learning model; generating, by the computing system, one or more mean-subtracted cardiac EGM strips by subtracting a mean of samples of the one or more temporally-modified cardiac EGM strips from the samples of the one or more temporally-modified cardiac EGM strips; computing, by the computing system, a moving signal envelope over a sliding window of the one or more mean-subtracted cardiac EGM strips; and normalizing, by the computing system, the one or more mean-subtracted cardiac EGM strips based on the moving signal envelope.

Example 4

The method of any of examples 1-3, wherein: the arrhythmia data is first arrhythmia data; the method further comprises: obtaining, by the computing system, a marker channel; preprocessing, by the computing system, the marker channel; applying, by the computing system, a marker channel-based deep learning model to the preprocessed marker channel to generate second arrhythmia data indicating a second set of occurrences of the one or more cardiac arrhythmias; determining, by the computing system, whether the first arrhythmia data and the second arrhythmia data are consistent; and at least one of: adjusting, by the computing system, a confidence level of an occurrence of one of the cardiac arrhythmias based on whether the occurrence of the cardiac arrhythmia is in both the first set of occurrences and the second set of occurrences or only in one of the first set of occurrences and the second set of occurrences, or extending, by the computing system, based on the occurrence of the cardiac arrhythmia being in both the first set of occurrences and the second set of occurrences, a duration of a monitoring session of a medical device that generates the one or more cardiac EGM strips.

Example 5

The method of example 4, wherein the marker channel indicates detected QRS complexes.

Example 6

The method of any of examples 1-5, wherein: preprocessing the one or more cardiac EGM strips comprises: scaling, by the computing system, the waveform represented by the one or more cardiac EGM strips; and decomposing, by the computing system, the waveform represented by the one or more cardiac EGM strips into a plurality of channels corresponding to different frequency bands, and applying the deep learning model to the one or more preprocessed cardiac EGM strips comprises applying, by the computing system, the deep learning model to the channels to generate the arrhythmia data.

Example 7

The method of any of examples 1-6, wherein: preprocessing the one or more cardiac EGM strips comprises: scaling, by the computing system, the waveform represented by the one or more cardiac EGM strips; and generating, by the computing system, a transformed waveform by transforming the scaled waveform into a 2-dimensional time-frequency domain, and applying the deep learning model to the one or more preprocessed cardiac EGM strips comprises applying the deep learning model to the transformed waveform.

Example 8

The method of any of examples 1-7, wherein: preprocessing the one or more cardiac EGM strips comprises applying, by the computing system, a learned scaling factor to the waveform represented by the one or more cardiac EGM strips, and applying the deep learning model comprises: determining, by the computing system, QRS probability values corresponding to a plurality of time points, each of the QRS probability values indicating a respective probability that a peak of a QRS complex occurs during the time point corresponding to the QRS probability value; and detecting, by the computing system, the set of occurrences of the one or more cardiac arrhythmias by providing the QRS probability values and the one or more preprocessed cardiac EGM strips as input to a neural network that generates the arrhythmia data.

Example 9

The method of any of examples 1-8, wherein preprocessing the one or more cardiac EGM strips comprises: determining, by the computing system, a polarity of the one or more cardiac EGM strips; and based on the polarity of the one or more cardiac EGM strips not being an expected polarity for the deep learning model, reversing, by the computing system, the polarity of the one or more cardiac EGM strips.

Example 10

The method of example 9, wherein: the deep learning model is a first deep learning model, and determining the polarity of the one or more cardiac EGM strips comprises applying, by the computing system, a second deep learning model to the one or more cardiac EGM strips to determine the polarity of the one or more cardiac EGM strips.

Example 11

The method of any of examples 1-10, wherein the method further comprises: obtaining, by the computing system, training input vectors, wherein each of the training input vectors comprises a segment of a training cardiac EGM strip and device classification data that indicate one or more cardiac arrhythmias detected in the training cardiac EGM strip; training, by the computing system, an autoencoder based on the training input vectors to reconstruct training cardiac EGM strips of the training input vectors; obtaining, by the computing system, additional device classification data; providing, by the computing system, the one or more preprocessed cardiac EGM strips and the additional device classification data to an input layer of the autoencoder; and determining, by the computing system, based on probability values generated by an intermediate layer of the autoencoder, whether the classification data correctly identifies cardiac arrhythmias, if any, in the preprocessed cardiac EGM strip, wherein each of the probability values corresponds to a different cardiac arrhythmia and indicates a level of confidence that the one or more preprocessed cardiac EGM strips contain the cardiac arrhythmia.

Example 12

The method of any of examples 1-11, wherein preprocessing the one or more cardiac EGM strips comprises one or more of: scaling samples of a signal of the one or more cardiac EGM strips such that the samples of the signal of the one or more cardiac EGM strips are distributed in an expected range of sample values for the deep learning model, or increasing or decreasing a sample rate of the signal of the one or more cardiac EGM strips to match an expected sample rate of the deep learning model.

Example 13

A computing system comprising: a storage device configured to store one or more cardiac electrogram (EGM)

strips that represent a waveform of a cardiac rhythm of a patient; one or more processing circuits configured to: preprocess the one or more cardiac EGM strips; and apply a deep learning model to the one or more preprocessed cardiac EGM strips to generate arrhythmia data indicating whether the one or more cardiac EGM strips represent one or more occurrences of one or more cardiac arrhythmias.

Example 14

The computing system of example 13, further configured to perform the methods of any of examples 2-12.

Example 15

A computer-readable storage medium having instructions stored thereon that, when executed, cause a computing system to perform the methods of any of examples 1-12.

Example 16

A method as described in the specification.

In some examples, the techniques of the disclosure include a system that comprises means to perform any method described herein. In some examples, the techniques of the disclosure include a computer-readable medium comprising instructions that cause processing circuitry to perform any method described herein.

It should be understood that various aspects and examples disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module, unit, or circuit for purposes of clarity, it should be understood that the techniques of this disclosure may be performed by a combination of units, modules, or circuitry associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" or "processing circuitry" as used herein may refer to any of the foregoing structure or any other physical structure suitable for implementation of the described techniques. Also, the techniques could be fully implemented in one or more circuits or logic elements.

Various examples have been described. These and other examples are within the scope of the following claims.

What is claimed is:

1. A method comprising:
obtaining, by a computing system, training input vectors, wherein each of the training input vectors comprises a segment of a training cardiac electrogram (EGM) strip and first classification data, wherein the first classification data identifies which of one or more classes of cardiac arrhythmias were detected in the training cardiac EGM strip;
training, by the computing system, an autoencoder based on the training input vectors to reconstruct training cardiac EGM strips of the training input vectors, wherein the autoencoder is a deep neural network that includes an input layer, a set of hidden layers, and an output layer, wherein the input layer of the autoencoder receives the training cardiac EGM strips of the training input vectors and the first classification data, the output layer of the auto-encoder outputs the reconstructed training cardiac EGM strips, and the hidden layers include an intermediate layer;
obtaining, by the computing system, one or more cardiac EGM strips that represent a waveform of a cardiac rhythm of a patient;
preprocessing, by the computing system, the one or more cardiac EGM strips;
applying, by the computing system, a deep learning model to the one or more preprocessed cardiac EGM strips to generate second classification data, wherein the second classification data identifies one or more classes of cardiac arrhythmias;
providing, by the computing system, the one or more preprocessed cardiac EGM strips and the second classification data to the input layer of the autoencoder; and
determining, by the computing system, based on probability values generated by the intermediate layer of the autoencoder, whether the second classification data correctly identifies the cardiac arrhythmias of the patient in the one or more preprocessed cardiac EGM strips,
wherein each of the probability values corresponds to a different cardiac arrhythmia and indicates a level of confidence that the one or more preprocessed cardiac EGM strips contain the cardiac arrhythmia.

2. The method of claim 1, wherein:
the second classification data identifies a first set of one or more occurrences of the one or more classes of cardiac arrhythmias,
the second classification data is first arrhythmia data, and the method further comprises:
obtaining, by the computing system, a marker channel;
preprocessing, by the computing system, the marker channel;
applying, by the computing system, a marker channel-based deep learning model to the preprocessed marker channel to generate second arrhythmia data indicating a second set of occurrences of the one or more classes of cardiac arrhythmias of the patient;
determining, by the computing system, whether the first arrhythmia data and the second arrhythmia data are consistent; and
at least one of:
adjusting, by the computing system, a confidence level of an occurrence of one of the cardiac arrhythmias of the patient based on whether the occurrence of the cardiac arrhythmia is in both the first set of occurrences and the second set of occurrences or only in one of the first set of occurrences and the second set of occurrences, or extending, by the computing system, based on the occurrence of the cardiac arrhythmia being in both the first set of occurrences and the second set of occurrences, a duration of a monitoring session of a medical device that generates the one or more cardiac EGM strips.

3. The method of claim 2, wherein the marker channel indicates detected QRS complexes.

4. The method of claim 1, wherein preprocessing the one or more cardiac EGM strips comprises:

determining, by the computing system, a polarity of the one or more cardiac EGM strips; and based on the polarity of the one or more cardiac EGM strips not being an expected polarity for the deep learning model, reversing, by the computing system, the polarity of the one or more cardiac EGM strips.

5. The method of claim 4, wherein:

the deep learning model is a first deep learning model, and determining the polarity of the one or more cardiac EGM strips comprises applying, by the computing system, a second deep learning model to the one or more cardiac EGM strips to determine the polarity of the one or more cardiac EGM strips.

6. The method of claim 1, wherein preprocessing the one or more cardiac EGM strips comprises:

generating, by the computing system, one or more temporally-modified cardiac EGM strips by modifying a temporal resolution of the one or more cardiac EGM strips to match an expected temporal resolution of a deep learning model; and generating, by the computing system, one or more preprocessed cardiac EGM strips by subtracting a mean of samples of the one or more temporally-modified cardiac EGM strips from the samples of the one or more temporally-modified cardiac EGM strips.

7. The method of claim 1, wherein preprocessing the one or more cardiac EGM strips comprises:

generating, by the computing system, one or more temporally-modified cardiac EGM strips by modifying a temporal resolution of the one or more cardiac EGM strips to match an expected temporal resolution of the deep learning model;

generating, by the computing system, one or more mean-subtracted cardiac EGM strips by subtracting a mean of samples of the one or more temporally-modified cardiac EGM strips from the samples of the one or more temporally-modified cardiac EGM strips;

computing, by the computing system, a moving signal envelope over a sliding window of the one or more mean-subtracted cardiac EGM strips; and normalizing, by the computing system, the one or more mean-subtracted cardiac EGM strips based on the moving signal envelope.

8. The method of claim 1, wherein:

preprocessing the one or more cardiac EGM strips comprises:

scaling, by the computing system, the waveform represented by the one or more cardiac EGM strips; and decomposing, by the computing system, the waveform represented by the one or more cardiac EGM strips into a plurality of channels corresponding to different frequency bands, and applying the deep learning model to the one or more preprocessed cardiac EGM strips comprises applying, by the computing system, the deep learning model to the channels to generate the second classification data.

9. The method of claim 1, wherein:

preprocessing the one or more cardiac EGM strips comprises:

scaling, by the computing system, the waveform represented by the one or more cardiac EGM strips; and generating, by the computing system, a transformed waveform by transforming the scaled waveform into a 2-dimensional time-frequency domain, and applying the deep learning model to the one or more preprocessed cardiac EGM strips comprises applying the deep learning model to the transformed waveform.

10. The method of claim 1, wherein:

preprocessing the one or more cardiac EGM strips comprises applying, by the computing system, a learned scaling factor to the waveform represented by the one or more cardiac EGM strips, and applying the deep learning model comprises:

determining, by the computing system, QRS probability values corresponding to a plurality of time points, each of the QRS probability values indicating a respective probability that a peak of a QRS complex occurs during the time point corresponding to the QRS probability value; and detecting, by the computing system, the set of occurrences of the one or more cardiac arrhythmias of the patient by providing the QRS probability values and the one or more preprocessed cardiac EGM strips as input to a neural network that generates the second classification data.

11. The method of claim 1, wherein preprocessing the one or more cardiac EGM strips comprises one or more of:

scaling samples of a signal of the one or more cardiac EGM strips such that the samples of the signal of the one or more cardiac EGM strips are distributed in an expected range of sample values for the deep learning model, or increasing or decreasing a sample rate of the signal of the one or more cardiac EGM strips to match an expected sample rate of the deep learning model.

12. The method of claim 1, wherein training the autoencoder comprises pretraining, by the computing system, layers of the autoencoder up through the intermediate layer of the autoencoder separately from subsequent layers of the autoencoder.

13. A computing system comprising:

a non-transitory storage device configured to store one or more cardiac electrogram (EGM) strips that represent a waveform of a cardiac rhythm of a patient; and one or more processing circuits embodied in hardware, the one or more processing circuits configured to:

obtain training input vectors, wherein each of the training input vectors comprises a segment of a training cardiac electrogram (EGM) strip and first classification data, wherein the first classification data identifies which of one or more classes of cardiac arrhythmias were detected in the training cardiac EGM strip;

train an autoencoder based on the training input vectors to reconstruct training cardiac EGM strips of the training input vectors, wherein the autoencoder is a deep neural network that includes an input layer, a set of hidden layers, and an output layer, wherein the input layer of the auto-encoder receives the training cardiac EGM strips of the training input vectors and the first classification data, the output layer of the auto-encoder outputs the reconstructed training cardiac EGM strips, and the hidden layers include an intermediate layer;

preprocess the one or more cardiac EGM strips;

apply a deep learning model to the one or more preprocessed cardiac EGM strips to generate second classification data, wherein the second classification data identifies one or more classes of cardiac arrhythmias;

provide the one or more preprocessed cardiac EGM strips and the second classification data to the input layer of the autoencoder; and determine, based on probability values generated by the intermediate layer of the autoencoder, whether the second classification data correctly identifies the cardiac arrhythmias of the patient in the one or more preprocessed cardiac EGM strips, wherein each of the probability values corresponds to a different cardiac arrhythmia and indicates a level of confidence that the one or more preprocessed cardiac EGM strips contain the cardiac arrhythmia.

14. The computing system of claim 13, wherein:
the second classification data identifies a first set of one or more occurrences of the one or more classes of cardiac arrhythmias,
the second classification data is first arrhythmia data;
the one or more processing circuits are further configured to:
obtain a marker channel;
preprocess the marker channel;
apply a marker channel-based deep learning model to the preprocessed marker channel to generate second arrhythmia data indicating a second set of occurrences of the one or more classes of cardiac arrhythmias of the patient;
determine whether the first arrhythmia data and the second arrhythmia data are consistent; and
at least one of:
adjust a confidence level of an occurrence of one of the cardiac arrhythmias of the patient based on whether the occurrence of the cardiac arrhythmia is in both the first set of occurrences and the second set of occurrences or only in one of the first set of occurrences and the second set of occurrences, or
extend, based on the occurrence of the cardiac arrhythmia being in both the first set of occurrences and the second set of occurrences, a duration of a monitoring session of a medical device that generates the one or more cardiac EGM strips.

15. The computing system of claim 14, wherein the marker channel indicates detected QRS complexes.

16. The computing system of claim 13, wherein the one or more processing circuits are configured such that, as part of preprocessing the one or more cardiac EGM strips, the one or more processing circuits:
determine a polarity of the one or more cardiac EGM strips; and
based on the polarity of the one or more cardiac EGM strips not being an expected polarity for the deep learning model, reverse the polarity of the one or more cardiac EGM strips.

17. The computing system of claim 16, wherein:
the deep learning model is a first deep learning model, and
the one or more processing circuits are configured such that, as part of determining the polarity of the one or more cardiac EGM strips, the one or more processing circuits apply a second deep learning model to the one or more cardiac EGM strips to determine the polarity of the one or more cardiac EGM strips.

18. The computing system of claim 13, wherein the one or more processing circuits are configured such that, as part of preprocessing the one or more cardiac EGM strips, the one or more processing circuits:
generate one or more temporally-modified cardiac EGM strips by modifying a temporal resolution of the one or more cardiac EGM strips to match an expected temporal resolution of a deep learning model; and
generate one or more preprocessed cardiac EGM strips by subtracting a mean of samples of the one or more temporally-modified cardiac EGM strips from the samples of the one or more temporally-modified cardiac EGM strips.

19. The computing system of claim 13, wherein the one or more processing circuits are configured such that, as part of preprocessing the one or more cardiac EGM strips, the one or more processing circuits:
generate one or more temporally-modified cardiac EGM strips by modifying a temporal resolution of the one or more cardiac EGM strips to match an expected temporal resolution of the deep learning model;
generate one or more mean-subtracted cardiac EGM strips by subtracting a mean of samples of the one or more temporally-modified cardiac EGM strips from the samples of the one or more temporally-modified cardiac EGM strips;
compute a moving signal envelope over a sliding window of the one or more mean-subtracted cardiac EGM strips; and
normalize the one or more mean-subtracted cardiac EGM strips based on the moving signal envelope.

20. The computing system of claim 13, wherein:
the one or more processing circuits are configured such that, as part of preprocessing the one or more cardiac EGM strips, the one or more processing circuits:
scale the waveform represented by the one or more cardiac EGM strips; and
decompose the waveform represented by the one or more cardiac EGM strips into a plurality of channels corresponding to different frequency bands, and
the one or more processing circuits are configured such that, as part of applying the deep learning model to the one or more preprocessed cardiac EGM strips, the one or more processing circuits apply the deep learning model to the channels to generate the second classification data.

21. The computing system of claim 13, wherein:
the one or more processing circuits are configured such that, as part of preprocessing the one or more cardiac EGM strips, the one or more processing circuits:
scale the waveform represented by the one or more cardiac EGM strips; and
generate a transformed waveform by transforming the scaled waveform into a 2-dimensional time-frequency domain, and
the one or more processing circuits are configured such that, as part of applying the deep learning model to the one or more preprocessed cardiac EGM strips, the one or more processing circuits apply the deep learning model to the transformed waveform.

22. The computing system of claim 13, wherein:
the one or more processing circuits are configured such that, as part of preprocessing the one or more cardiac EGM strips, the one or more processing circuits apply a learned scaling factor to the waveform represented by the one or more cardiac EGM strips, and the one or more processing circuits are configured such that, as part of applying the deep learning model, the one or more processing circuits:

determine QRS probability values corresponding to a plurality of time points, each of the QRS probability values indicating a respective probability that a peak of a QRS complex occurs during the time point corresponding to the QRS probability value; and detect the set of occurrences of the one or more cardiac arrhythmias of the patient by providing the QRS probability values and the one or more preprocessed cardiac EGM strips as input to a neural network that generates the second classification data.

23. The computing system of claim 13, wherein the one or more processing circuits are configured such that, as part of preprocessing the one or more cardiac EGM strips, the one or more processing circuits are configured to:

scale samples of a signal of the one or more cardiac EGM strips such that the samples of the signal of the one or more cardiac EGM strips are distributed in an expected range of sample values for the deep learning model, or increase or decrease a sample rate of the signal of the one or more cardiac EGM strips to match an expected sample rate of the deep learning model.

24. The computing system of claim 13, wherein the one or more processing circuits are configured to, as part of training the autoencoder, pretrain layers of the autoencoder up through the intermediate layer of the autoencoder separately from subsequent layers of the autoencoder.

25. A non-transitory computer-readable storage medium having instructions stored thereon that, when executed, cause a computing system to:

obtain training input vectors, wherein each of the training input vectors comprises a segment of a training cardiac electrogram (EGM) strip and first classification data, wherein the first classification data identifies which of one or more classes of cardiac arrhythmias were detected in the training cardiac EGM strip;

train an autoencoder based on the training input vectors to reconstruct training cardiac EGM strips of the training input vectors, wherein the autoencoder is a deep neural network includes an input layer, a set of hidden layers, and an output layer, wherein the input layer of the auto-encoder receives the training cardiac EGM strips of the training input vectors and the first classification data, the output layer of the auto-encoder outputs the reconstructed training cardiac EGM strips, and the hidden layers include an intermediate layer;

obtain one or more cardiac EGM strips that represent a waveform of a cardiac rhythm of a patient;

preprocess the one or more cardiac EGM strips;

apply a deep learning model to the one or more preprocessed cardiac EGM strips to generate second classification data, wherein the second classification data identifies one or more classes of cardiac arrhythmias;

provide the one or more preprocessed cardiac EGM strips and the second classification data to the input layer of the autoencoder; and determine, based on probability values generated by the intermediate layer of the autoencoder, whether the second classification data correctly identifies the cardiac arrhythmias of the patient in the one or more preprocessed cardiac EGM strips, wherein each of the probability values corresponds to a different cardiac arrhythmia and indicates a level of confidence that the one or more preprocessed cardiac EGM strips contain the cardiac arrhythmia.

* * * * *